(12) United States Patent
Young et al.

(10) Patent No.: US 8,738,397 B2
(45) Date of Patent: May 27, 2014

(54) DISTRIBUTED RANDOMIZATION AND SUPPLY MANAGEMENT IN CLINICAL TRIALS

(75) Inventors: Benjamin Young, Manlius, NY (US); Glen de Vries, New York, NY (US); David Fenster, Jersey City, NJ (US); Jonathan Lebowitsch, Brooklyn, NY (US)

(73) Assignee: Medidata Solutions, Inc., New York, NY (US)

( * ) Notice: Subject to any disclaimer, the term of this patent is extended or adjusted under 35 U.S.C. 154(b) by 74 days.

(21) Appl. No.: 13/157,875

(22) Filed: Jun. 10, 2011

(65) Prior Publication Data

US 2011/0307267 A1  Dec. 15, 2011

Related U.S. Application Data

(60) Provisional application No. 61/354,200, filed on Jun. 12, 2010.

(51) Int. Cl.
*G06Q 10/00* (2012.01)
*G06Q 50/00* (2012.01)

(52) U.S. Cl.
USPC .......................................................... 705/2

(58) Field of Classification Search
CPC ...... G06Q 50/22; G06Q 50/24; G06F 19/322; G06F 19/324
USPC ............................. 705/2, 3; 707/999; 715/700
See application file for complete search history.

(56) References Cited

U.S. PATENT DOCUMENTS

| | | | |
|---|---|---|---|
| 5,898,586 A * | 4/1999 | Jeatran et al. ...................... | 705/2 |
| 7,054,823 B1 * | 5/2006 | Briegs et al. ....................... | 705/2 |
| 7,647,235 B1 * | 1/2010 | Fava et al. .......................... | 705/2 |
| 8,185,608 B1 * | 5/2012 | York et al. ..................... | 709/218 |
| 2004/0249664 A1 * | 12/2004 | Broverman et al. .............. | 705/2 |
| 2005/0075832 A1 | 4/2005 | Ikeguchi et al. | |
| 2008/0046469 A1 * | 2/2008 | Ikeguchi et al. ........... | 707/104.1 |
| 2008/0162229 A1 * | 7/2008 | Moore .............................. | 705/7 |
| 2009/0313048 A1 * | 12/2009 | Kahn et al. ........................ | 705/3 |

OTHER PUBLICATIONS

Simon, Richard. Restricted Randomization Designs in Clinical Trials. Biometrics, Jun. 1979, vol. 35, No. 2, p. 503-512.*
Bellaire, Gunter, Jaynes, Kevin, and Byrom, Bill. The eClinical Core. European Pharmaceutical Contractor, Dec. 2008, p. 84-88.*

(Continued)

*Primary Examiner* — Elaine Gort
*Assistant Examiner* — Jonathan Durant
(74) *Attorney, Agent, or Firm* — Hoffmann & Baron, LLP

(57) ABSTRACT

A distributed clinical trial system that provides configurability, reusability and integration of randomization and inventory configurations for different clinical trials with various electronic data capture (EDC) systems. The distributed clinical trial system includes a method of randomizing subjects in a multi-arm clinical trial. In accordance with a method, a subject identifier and a trial identifier are received from an EDC system. The trial identifier indicates the multi-arm clinical trial and the subject identifier indicates a subject enrolled in the multi-arm clinical trial. A randomization design previously configured for the multi-arm clinical trial is retrieved from a database based on the received trial identifier. The subject identifier is assigned to an arm identifier of the multi-arm clinical trial based on the randomization design. The arm identifier indicates an arm of the multi-arm clinical trial to which the subject has been assigned.

33 Claims, 27 Drawing Sheets

(56) References Cited

OTHER PUBLICATIONS

McEntegart, Damian, Case Studies Using Dynamic Randomisation Techniques other than Minimisation, EFSPI meeting on Adaptive Randomisation, Dec. 7, 2006.*

McEntegart, Damian J. "The pursuit of balance using stratified and dynamic randomization techniques: an overview." Drug Information Journal 37.3 (2003): 293-308.*

Simon, Richard, "Restricted Randomization Designs in Clinical Trials", Biometrics, vol. 35, No. 2, Jun. 1979, pp. 503-512.

Ji, Yuan, et al., "Adaptive randomization for multi-arm comparative clinical trials based on joint efficacy/toxicity outcomes", Biometrics, Sep. 2009, vol. 65, Iss. 3, pp. 876-884.

Freidlin, Boris, et al., "Multi-Arm Clinical Trials of New Agents: Some Design Considerations", Clinical Cancer Research, published online Jul. 15, 2008, vol. 14, pp. 4368-4371.

Shen, David, et al., "Randomization in Clinical Trial Studies", Datasheet (online). AstraZenica Pharmaceuticals, Aug. 2006.

Written Opinion and Search Report issued on Oct. 24, 2011 in International Application No. PCT/US2011/039989.

* cited by examiner

| Study List | Design | Sites and Subjects | Inventory | Logistics | Properties |

Balance Study 1

| Randomization Design | Simulation Setup | Simulation Results | Treatment Design | 📄 Configuration Report |

Study Design                                                                 ✓ Save Design Study Arms                          + Add Arm

| Ratio | Name |
|---|---|
| 2 | Control Group |
| 3 | Demophyne 10mg |
| 3 | Demophyne 20mg |

Randomization Factors              + Add Factor

| Weight | Factor | Values |
|---|---|---|
| 1 | Site | N/A |
| 1 | Stratum | Demophyne 10mg |
| 1 | Study | |
| 1 | Age Group | between 18 and 45 years old, between 45 and 65 years old, 65 years old and over |
| 1 | Sex | Male, Female |

General

Randomization Second Best: Probability (%)

15

Strata between 18 and 45 years old, Male
between 45 and 65 years old, Male
65 years old and over, Male
between 18 and 45 years old, Female
between 45 and 65 years old, Female
65 years old and over, Female

FIG. 11

| Study List | Design | Sites and Subjects | Inventory | Logistics | Properties |

Balance Study 1

| Randomization Design | Simulation Setup | Simulation Results | Treatment Design |  🗋 Configuration Report |

Simulation Setup List                                       ✓ New Simulation Setup

| Name | Number of Run | Number of Subjects | Number of Sites | Strata Distriution Ratios | Actions |
|---|---|---|---|---|---|
| sdf | 5 | 20 | 2 | between 18 and 45 years old, Male (1)<br>between 45 and 65 years old, Male (1)<br>65 years old and over, Male (1)<br>between 18 and 45 years old, Female (1)<br>between 45 and 65 years old, Female (1)<br>65 years old and over, Female (1) | Execute This Simulation   Edit<br>Show Results (last execution) |

FIG. 12

| Randomization Design | Simulation Setup | Simulation Results | Treatment Design |

Simulation Execution Details (start time: 02-23-2011 11:46:45 PM UTC})

Randomization Design Parameters (show)    Back to Analysis

Simulation Setup Parameters (show)

Run Number 1                              *# of Subjects (Imbalance)*

| Study Balance | S2A1: 1 | S2A2: 1 | Total |
|---|---|---|---|
|  | 10 (0.0) | 10 (0.0) | 20 |

*# of Subjects (Imbalance)*

| Site Balance | S2A1: 1 | S2A2: 1 | Total |
|---|---|---|---|
| Site 1 | 4 (0.0) | 4 (0.0) | 8 |
| Site 2 | 6 (0.0) | 6 (0.0) | 12 |

*# of Subjects (Imbalance)*

| State Balance | S2A1: 1 | S2A2: 1 | Total |
|---|---|---|---|
| Fac2: f2s1 | 5 (0.5) | 6 (0.5) | 11 |
| Fac2: f2s2 | 6 (0.5) | 4 (0.5) | 9 |

*# of Subjects (Imbalance)*

| Strata Balance | S2A1: 1 | S2A2: 1 | Total |
|---|---|---|---|
| f2s1 | 6 (0.5) | 6 (0.5) | 11 |

*FIG. 14A*

| Randomization Design | Simulation Setup | Simulation Results | Treatment Design |

Simulation Execution Details (start time: 02-23-2011 11:46:45 PM UTC})

Randomization Design Parameters (show)        Show Detailed Results

Simulation Setup Parameters (show)

View tables:
Means and Standard Deviations | Minima | Runs Out of Balance |

*Mean # of Subjects +/- Standard Deviation*

| Study Means | S2A1: 1 | S2A2: 1 |
|---|---|---|
|  | 10.0 +/- 0.0 | 10.0 +/- 0.0 |

*Mean # of Subjects +/- Standard Deviation*

| Site Means | S2A1: 1 | S2A2: 1 |
|---|---|---|
| Site 1 | 4.6 +/- 1.62 | 4.8 +/- 0.98 |
| Site 2 | 5.4 +/- 1.52 | 5.2 +/- 0.98 |

*Mean # of Subjects +/- Standard Deviation*

| State Means | S2A1: 1 | S2A2: 1 |
|---|---|---|
| Fac2: f2s1 | 4.6 +/- 0.8 | 4.8 +/- 0.98 |
| Fac2: f2s2 | 5.4 +/- 0.8 | 5.2 +/- 0.98 |

*Mean # of Subjects +/- Standard Deviation*

| Strata Means | S2A1: 1 | S2A2: 1 |

*FIG. 14B*

Manage Article Type Demophyne 10mg x 30

Fields marked with an asterisk (*) are required.

Name*

Demophyne 10mg x 30

Minimal Number of Days Between Dispensing and Expiration*

35

Description

[ ✓ Save ]  [ ✗ Cancel ]  [ 🗑 Delete ]

FIG. 16

| Study List | Design | Sites and Subjects | Inventory | Logistics | Properties |

Balance Study 1

| Manage Subjects | Manage Sites |

Sites

| Name | Country | Depot | Supply Plan | Shipping Status | | |
|------|---------|-------|-------------|-----------------|---|---|
|      | None selected | None selected | None selected | None selected | ✓ Apply | ✗ Reset |

| Name | Number | Country | Depot | Supply Plan | # of Subject | # of Shipments | # of Inventory Items | Shipping Status |
|------|--------|---------|-------|-------------|--------------|----------------|----------------------|-----------------|
| ☐ Balance Study Site 1 | Number1 | USA | US Shipping Inc. | Med enrollers | 0 | 0 | 0 | Inactive |
| ☐ Balance Study Site 2 | Number3 | USA | | Med enrollers | 0 | 0 | 0 | Inactive |
| ☑ Balance Study Site 3 | Number5 | UK | UK Depot LTD. | Med enrollers | 0 | 1 | 10 | Active |
| ☐ Site 1 | | | | High Enrollers | 13 | 0 | 1 | Inactive |
| ☐ Site 2 | | | | High Enrollers | 7 | 0 | 0 | Inactive |

[ ✓ Assign Supply Plan ] [ ✓ Assign Depot ] [ ✓ Deactiviate Shipping ]

*FIG. 17A*

Choose Supply Plan for Sites in Study Demophyne for Focus Group               close [X]

Please choose a Supply Plan for the Sites you have selected.

◉ ▽ Med enrollers

| Article Types | Disp Exp (?) | Init Stock (?) | Threshold (?) | Level (?) |
|---|---|---|---|---|
| 30 x Placebo | 45 | 10 | 5 | 10 |
| 30 x active | 45 | 10 | 5 | 10 |

( ✓ Assign Supply Plan )  ( ✗ Cancel )

*FIG. 17B*

| Study List | Design | Sites and Subjects | Inventory | Logistics | Properties |

Balance Study 1

Manage Subjects | Manage Sites  ⇩ Download Subject List

Subjects (20)   Subject Distribution Report

Subject ID | Stratum | Factor State | Site
|  | None selected | None selected | None selected |  ✓ Apply   ✗ Reset

| Subject ID | Stratum | Site | Assigned Study Arm | Randomization Time |
|---|---|---|---|---|
| SIM 1 |  | Site 1 | Demophyne 10mg | 02-23-2011 11:46:51 PM UTC |
| SIM 2 |  | Site 1 | Control Group | 02-23-2011 11:46:51 PM UTC |
| SIM 3 |  | Site 1 | Control Group | 02-23-2011 11:46:51 PM UTC |
| SIM 4 |  | Site 1 | Demophyne 10mg | 02-23-2011 11:46:51 PM UTC |
| SIM 5 |  | Site 2 | Control Group | 02-23-2011 11:46:51 PM UTC |
| SIM 6 |  | Site 1 | Demophyne 10mg | 02-23-2011 11:46:51 PM UTC |
| SIM 7 |  | Site 1 | Control Group | 02-23-2011 11:46:51 PM UTC |
| SIM 8 |  | Site 1 | Demophyne 10mg | 02-23-2011 11:46:51 PM UTC |
| SIM 9 |  | Site 1 | Control Group | 02-23-2011 11:46:51 PM UTC |
| SIM 10 |  | Site 1 | Demophyne 10mg | 02-23-2011 11:46:51 PM UTC |

*FIG. 18*

| | | | | | | |
|---|---|---|---|---|---|---|
| Study List | Design | Sites and Subjects | Inventory | Logistics | Properties | |

Balance Study 1

| Manage Items | Manage Shipments | Manage Batches |
|---|---|---|

Shipments                                    ✓ Run Shipping Algorithm

| Name | Site | Status | Depot | | |
|------|------|--------|-------|---|---|
|      | None selected | None selected | None selected | ✓ Apply | ✗ Reset |

| Name | Status | Status Changed At | Site | Depot | Tracking Number | # of Inventory Items |
|------|--------|-------------------|------|-------|-----------------|---------------------|
| 1001 | Requested | 03-01-2011 05:57:12 PM UTC | Balance Study Site 3 | Depot3 | | 10 |

FIG. 19

| Study List | Design | Sites and Subjects | Inventory | Logistics | Properties |

Balance Study 1

| Manage Items | Manage Shippments | Manage Batchs | ⬇ Download Inventory Item List |

Inventory List (999)          Depot Inventory Report   Site Inventory Report

Item Number   Status           Site            Depot           Subject   Visit
[         ]   [None selected]  [None selected] [None selected] [     ]   [    ]   [✓ Apply] [✗ Reset]

Shipment          Inventory Batch   Article Type
[None selected]   [            ]    [None selected]

| Item Number | Number | Site | Depot | Subject | Visit | Shipment | Inventory Batch | Article Type | Sequence | Location |
|---|---|---|---|---|---|---|---|---|---|---|
| DMF 121001 | Reserved for Shipping | Balance Study Site 3 | Depot3 | | | 1001 | LOT CBF 2000988 | Asprin 10mg x 30 | 1001 | Isle 2 Rack 4 |
| DMF 121002 | Reserved for Shipping | Balance Study Site 3 | Depot3 | | | 1001 | LOT CBF 2000988 | Asprin 10mg x 30 | 1002 | Isle 2 Rack 4 |
| DMF 121003 | Reserved for Shipping | Balance Study Site 3 | Depot3 | | | 1001 | LOT CBF 2000988 | Asprin 10mg x 30 | 1003 | Isle 2 Rack 4 |
| DMF 121004 | Reserved for Shipping | Balance Study Site 3 | Depot3 | | | 1001 | LOT CBF 2000988 | Asprin 10mg x 30 | 1004 | Isle 2 Rack 4 |
| DMF 121005 | Reserved for Shipping | Balance Study Site 3 | Depot3 | | | 1001 | LOT CBF 2000987 | Demophyne 10 x 30 | 2001 | Isle 2 Rack 3 |
| DMF 121006 | Reserved for Shipping | Balance Study Site 3 | Depot3 | | | 1001 | LOT CBF 2000987 | Demophyne 10 x 30 | 2002 | Isle 2 Rack 3 |
| DMF 121007 | Reserved for Shipping | Balance Study Site 3 | Depot3 | | | 1001 | LOT CBF 2000988 | Asprin 10mg x 30 | 1005 | Isle 2 Rack 4 |
| DMF 121008 | Available at Depot | | Depot3 | | | | LOT CBF 2000988 | Asprin 10mg x 30 | 1006 | Isle 2 Rack 4 |
| DMF 121009 | Available at Depot | | Depot3 | | | | LOT CBF 2000988 | Asprin 10mg x 30 | 1007 | Isle 2 Rack 4 |
| DMF 1210010 | Reserved for Shipping | Balance Study Site 3 | Depot3 | | | 1001 | LOT CBF 2000987 | Demophyne 10 x 30 | 2003 | Isle 2 Rack 3 |

*FIG. 20*

| Study List | Design | Sites and Subjects | Inventory | Logistics | Properties |

Balance Study 1

| Manage Items | Manage Shipments | Manage Batches |

Inventory Batch List                                    √ New Inventory Batch

| Name | Article Types | Expiry Date | Additional Batch Identifier | Notes | Depot | # of Inventory Items |
|---|---|---|---|---|---|---|
| LOT CBF 200987 | Demophyne 10mg x 30 | 12 Feb 2013 | | | Depot3 | 477 |
| LOT CBF 200988 | Aspirin 10mg x 30 | 12 Feb 2013 | | | Depot3 | 522 |

*FIG. 21*

| Study List | Design | Sites and Subjects | Inventory | Logistics | Properties |

Balance Study 1

Supply Plan List                                               ✓ Add Supply Plan

Abbreviation Key                                                    (hide)

Disp Exp: Minimal number of days between         Threshold: Site restocking
dispensing and expiration                            threshold

Ship Exp: Minimal number of days between         Level: Site restocking level
shipping and expiration Init Stock: Initial site stocking level

| Supply Plan | Article Types | Disp Exp | Ship Exp | Init Stock | Threshold | Level | Sites |
|---|---|---|---|---|---|---|---|
| Med enrollers (default) | Demophyne 10mg x 30 | 35 | 100 | 5 | 3 | 5 | 3 |
| | Aspirin 10mg x 30 | 35 | 100 | 5 | 3 | 5 | |
| High Enrollers | Demophyne 10mg x 30 | 35 | 90 | 8 | 6 | 10 | 2 |
| | Aspirin 10mg x 30 | 35 | 90 | 8 | 6 | 10 | |

*FIG. 22*

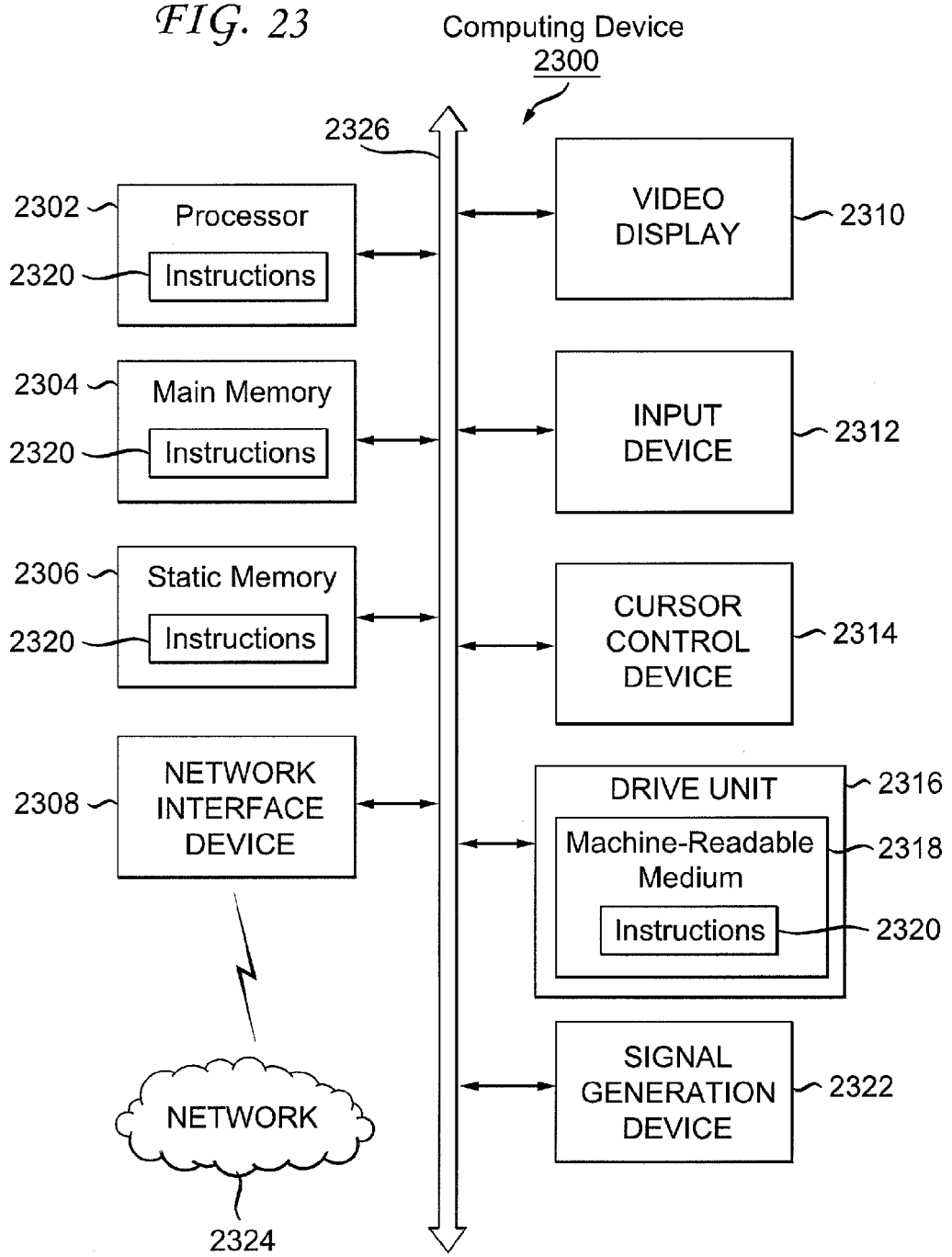

DISTRIBUTED RANDOMIZATION AND SUPPLY MANAGEMENT IN CLINICAL TRIALS

CROSS REFERENCE TO RELATED APPLICATION

This application claims priority to U.S. Provisional Application No. 61/354,200 filed on Jun. 12, 2010, which is incorporated herein by reference in its entirety.

BACKGROUND

1. Field of Technology

The present application relates generally to clinical trial systems. More specifically, the present application is directed to a distributed clinical trial system that provides configurability, reusability and integration of randomization and inventory management configurations for different clinical trials with various electronic data capture (EDC) systems.

2. Brief Description of Related Art

A clinical trial is performed to, among other things, test the safety and efficacy of a new drug or treatment (e.g., therapy), and ultimately, to ascertain whether or not a therapy is appropriate for widespread human consumption.

There are generally four phases in the clinical trial. In Phase I, a few subjects (approximately 20 to 100) are used to determine toxicity of the therapy. In Phase II, more subjects (approximately 20-300) are used to determine efficacy and further ascertain safety of the therapy. In Phase III, hundreds to thousands of subjects are used to obtain meaningful statistical analysis of the therapy's efficacy. The treatment may be compared to either a placebo or another existing therapy. In Phase IV (post-approval of clinical trial), more testing is performed to evaluate long-term effects and to evaluate other indications of the therapy.

In a comparative clinical trial, subjects are assigned to multiple arms in order to facilitate analysis in a comparative fashion. For example, subjects assigned to one arm (e.g., "control") can receive a placebo, while subjects assigned to another arm can receive the medication being tested. Comparing the results of the therapy in each arm of a multi-arm clinical trial provides a measure of the efficacy of the medication in testing the effectiveness of the medication. In another example, arms can also receive various dosages of the medication being tested to evaluate the safety and efficacy of the dosages. Still in other examples, some arms can receive another medication against which the safety and efficacy of the medication being tested can be evaluated.

The subjects of the multi-arm clinical trial are generally randomized (e.g., assigned to the arms of the multi-arm clinical trial in a random fashion) to avoid biases that may occur in the selection of subjects for the clinical trial. A bias can be introduced if a subject who is a particularly well-suited to respond to a new medication—based on certain prognostic factors (e.g., sex, age, prior condition or other factor)—is intentionally assigned to an arm that receives the medication being tested and not an arm that receives a placebo. This could skew the statistical analysis and the outcome of the clinical trial to favor the medication being tested.

A bias can further be introduced unintentionally if more subjects having certain prognostic factors are randomly, but unevenly, assigned to one arm versus another arm of the clinical trial. Some clinical trials have attempted to mitigate this bias by attempting to balance certain factors across the arms of the clinical trial.

To further mitigate the risk of bias, the multi-arm clinical trials are generally single-blinded or double-blinded. The single-blinded clinical trial does not reveal the arm assignment to the subject, while the double-blinded clinical trial does not reveal the arm assignment to the subject and to the investigator. Most randomized clinical trials are blinded.

There are currently a number of categories of computerized clinical trial management systems that facilitate different aspects of the clinical trial. A first category includes an interactive voice-response (IVR) system or interactive-web-response (IWR) system. Systems in this category typically facilitate enrolment of multiple subjects into a clinical trial and the dispensing of medication during the clinical trial. A second category includes an electronic data capture (EDC). Systems in this category typically capture clinical information concerning the subjects during the clinical trial.

In most clinical trials, the foregoing systems in these two categories are separate and not integrated. In some cases, where integration has been effected, the EDC receives information concerning the enrolled subjects from the IVR/IWR and randomizes the subjects into arms of the clinical trial. The EDC may also receive information from the IVR/IWR concerning medication that is administered to the subjects during visits of the clinical trial. The second system maintains the received information and other information concerning the clinical trial in a runtime database. Upon completion of the clinical trial, the maintained information is closed out and used to evaluate the medication tested in the clinical trial.

Typically, a designer writes a specification for the IVR or IWR according to the requirements of a particular clinical trial. Thereafter, a developer generally hard-codes or programs the IVR/IWR for the clinical trial in accordance with the specification. Subsequent revisions to the specification of the clinical trial require recoding of the IVR/IWR. While there has been some integration in clinical trial management, a clinical trial management system that enables configurability, reusability and integration of randomization and dispensing of medication across different trials and various EDCs has remained illusive.

SUMMARY

In accordance with an embodiment, a method of randomizing subjects in a multi-arm clinical trial is disclosed. In the method, a subject identifier and a trial identifier are received from an electronic data capture (EDC) system. The trial identifier indicates the multi-arm clinical trial and the subject identifier indicates a subject enrolled in the multi-arm clinical trial. A randomization design previously configured for the multi-arm clinical trial is retrieved from a database based on the received trial identifier. The subject identifier is assigned to an arm identifier of the multi-arm clinical trial based on the randomization design. The arm identifier indicates an arm of the multi-arm clinical trial to which the subject has been assigned.

In accordance with an embodiment, a method of dispensing medication in a multi-arm clinical trial is disclosed. In the method a subject identifier and a trial identifier are received from an electronic data capture (EDC) system. The trial identifier indicates the multi-arm clinical trial and the subject identifier indicates a subject enrolled in the multi-arm clinical trial. An arm identifier is retrieved from a database based on the received subject identifier. The arm identifier indicates an arm in the multi-arm clinical trial to which the subject is assigned. A treatment for the arm identifier is determined based on a treatment design previously configured for the multi-arm clinical trial. The treatment includes a set of one or more units of at least one article type.

In accordance with yet another embodiment, a system to randomize subjects in a multi-arm clinical trial is disclosed. The system includes a randomizer configured to receive a subject identifier and a trial identifier from an electronic data capture (EDC) system, the trial identifier indicating the multi-arm clinical trial. The subject identifier indicates a subject enrolled in the multi-arm clinical trial. The randomizer is further configured to retrieve randomization design previously configured for the multi-arm clinical trial from a database based on the received trial identifier. The randomizer is also configured to assign the subject identifier to an arm identifier of the multi-arm clinical trial based on the randomization design. The arm identifier indicates an arm of the multi-arm clinical trial to which the subject has been assigned.

In accordance with a further embodiment, a system to dispense medication in a multi-arm clinical trial is disclosed. The system includes an article dispenser configured to receive a subject identifier and a trial identifier from an electronic data capture (EDC) system, the trial identifier indicating the multi-arm clinical trial. The subject identifier indicates a subject enrolled in the multi-arm clinical trial. The article dispenser is further configured to retrieve an arm identifier from a database based on the received subject identifier. The arm identifier indicates an arm in the multi-arm clinical trial to which the subject is assigned. The article dispenser is also configured to determine treatment for the arm identifier based on a treatment design previously configured for the multi-arm clinical trial. The treatment includes a set of one or more units of at least one article type.

In accordance with another embodiment, a machine-readable storage medium is disclosed. The machine-readable storage medium includes operational instructions that, when executed by a processor, cause the processor to receive a subject identifier and a trial identifier from an electronic data capture (EDC) system. The trial identifier indicates a multi-arm clinical trial and the subject identifier indicates a subject enrolled in the multi-arm clinical trial. The machine-readable storage medium further includes operational instructions that cause the processor to retrieve a randomization design previously configured for the multi-arm clinical trial from a database based on the received trial identifier. The machine-readable storage medium also includes operational instructions that cause the processor to assign the subject identifier to an arm identifier of the multi-arm clinical trial based on the randomization design. The arm identifier indicates an arm of the multi-arm clinical trial to which the subject has been assigned.

In accordance with still another embodiment, a machine-readable storage medium. The machine-readable storage medium includes operational instructions that, when executed by a processor, cause the processor to receive a subject identifier and a trial identifier from an electronic data capture (EDC) system. The trial identifier indicatives a multi-arm clinical trial and the subject identifier indicates a subject enrolled in the multi-arm clinical trial. The machine-readable storage medium further includes operational instructions that cause the processor to retrieve an arm identifier from a database based on the received subject identifier. The arm identifier indicates an arm in the multi-arm clinical trial to which the subject is assigned. The machine-readable storage medium also includes operational instructions that cause the processor to determine treatment for the arm identifier based on a treatment design previously configured for the multi-arm clinical trial. The treatment includes a set of one or more units of at least one article type.

These and other purposes, goals and advantages of the present application will become apparent from the following detailed description of example embodiments read in connection with the accompanying drawings.

BRIEF DESCRIPTION OF THE DRAWINGS

Some embodiments are illustrated by way of example and not limitation in the figures of the accompanying drawings in which:

FIG. 11 illustrates an example webpage to configure a randomization design for a clinical trial;

FIG. 12 illustrates an example webpage to setup and simulate a randomization design for a clinical trial;

FIG. 14A illustrates an example webpage to display overall clinical trial balance of subject assignments and balance of subject assignment in trial sites for a simulation;

FIG. 14B illustrates an example webpage to display aggregate statistical results across runs of a randomization simulation;

FIG. 16 illustrates an example webpage to manage article types illustrated in FIG. 15;

FIG. 17A illustrates an example webpage generated for trial sites in a clinical trial to manage or more trial sites;

FIG. 17B illustrates an example webpage to assign a supply plan to one or more selected trial sites of the clinical trial;

FIG. 18 illustrates an example webpage generated for management of subjects in a clinical trial;

FIG. 19 illustrates an example webpage for management of article shipments in a clinical trial;

FIG. 20 illustrates an example webpage for managing items of inventory in a clinical trial;

FIG. 21 illustrates an example webpage for managing an inventory batch list in a clinical trial;

FIG. 22 illustrates an example webpage for managing logistics supply plan list; and FIG. 23 is a block diagram of a general computer system.

DETAILED DESCRIPTION

A distributed clinical trial system and methods are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

Figure 1:
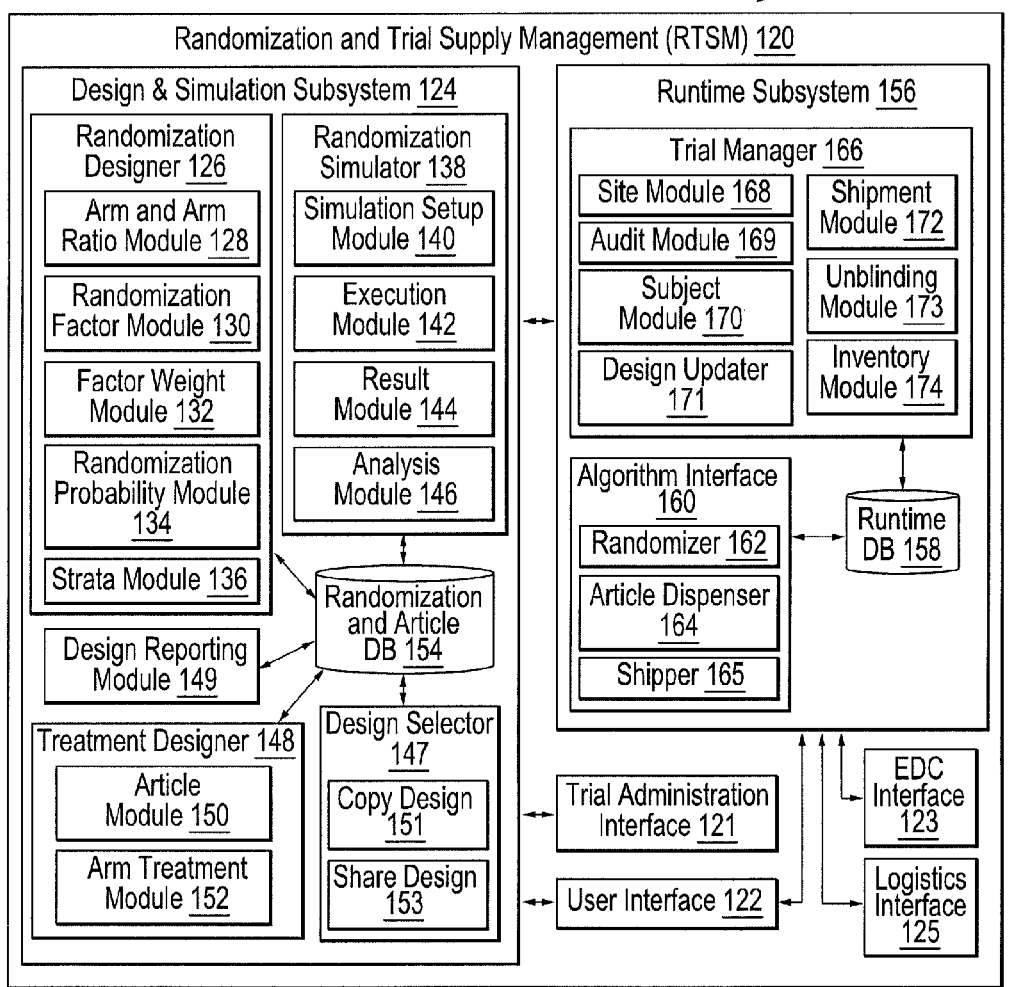
FIG. 1 illustrates a block diagram of an example clinical trial system configured to design, simulate and run at least one clinical trial.
Figure 1:
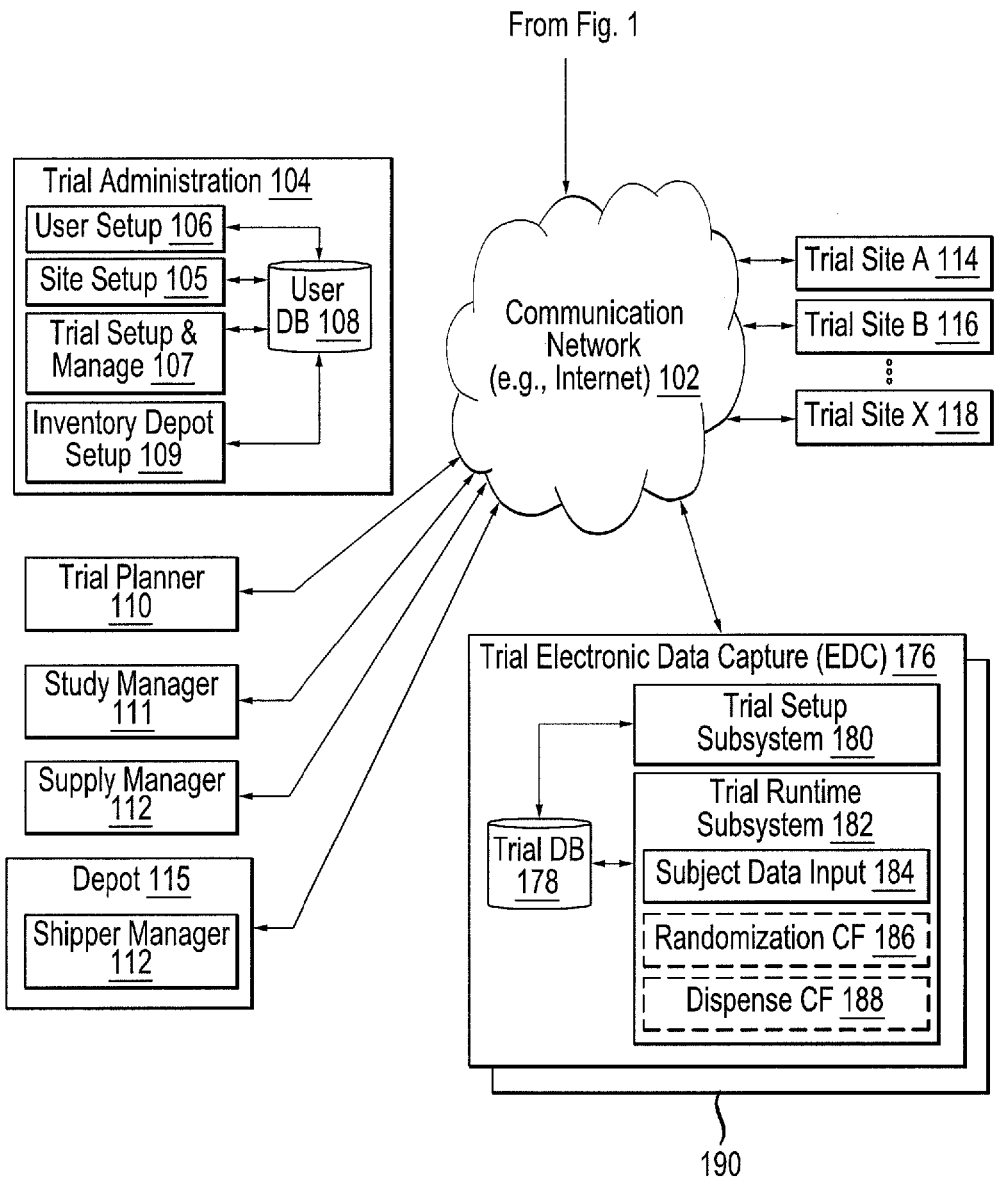

FIG. 1 illustrates a block diagram of an example clinical trial system 100 configured to design, simulate and run at least one clinical trial. For brevity and conciseness, the following description will describe the design, simulation and execution of an example clinical trial. It should be noted that multiple clinical trials can be designed, simulated and executed, whether contemporaneously or sequentially, in a similar fashion described hereinafter.

The clinical trial system 100 includes a trial administration system 104, randomization and trial supply management (RTSM) system 120, and at least one electronic data capture system (EDC) 176, 190. The clinical trial system can also include a trial planner 110, study manager 111, supply manager 112, at least one at least one depot 115 having a shipper manager 113, and a plurality of trial sites 114, 116, 118. The trial planner 110, study manager 111, supply manager 112, shipper manager 113, and trial sites 114, 118, 118 can be implemented or operated with respective computing devices. A communication network 102 interconnects the foregoing systems 104, 120, 176 and computing devices 110-118 in the clinical trial system 100.

The communication network 102 is configured to transmit one or more messages associated with clinical trial system 100. The transmission over the communication network 102 can be accomplished, for example, via Transfer Control Protocol/Internet Protocol (TCP/IP), User Datagram Protocol (UDP)/IP, Hypertext Transfer Protocol (HTTP), File Transfer Protocol (FTP), as well as any combination of conventional protocols or protocols deployed in the future.

The computing devices 110-118 can include personal computers that are configured to communicate via the communication network 102 in order to transmit and receive information concerning the clinical trial. The computing devices 102 can include clients (e.g., Internet Explorer®), which can execute one or more applications and display one or more web pages associated with the clinical trial system 100. The web pages can be displayed via hypertext markup language (HTML), extensible markup language (XML), extensible HTML, and/or other markup languages, as well as any other technology now available or to be deployed in the future.

The trial administration system 104 is a centralized system that is configured to enable a trial planner (e.g., contract research organization) 110 to setup and manage a clinical trial as well as sites and users associated with the trial sites 114, 116, 118. It should be noted the clinical trial system 100 is configured to support multiple trial planners 110, as well as the setup and management of multiple clinical trials and their associated sites and users.

The trial administration system 104 includes a site setup module 105, user setup module 106, trial setup and manage module 107, inventory depot setup module 109, and user database 108. The trial setup and manage module 107 is configured to enable the trial planner 110 to create and manage the clinical trial in the clinical trial system 100 in the RTSM system 120 and/or the EDC system 176, as will be described in greater detail below with reference to the RTSM system 120 and the EDC system 176. At setup, the trial setup and manage module 107 is configured to generate a trial ID associated with clinical trial and to transmit the trial ID, site IDs (set up via site setup 105) to the RTSM system 120 and the EDC system 176.

The trial administration system 104 is further configured to authenticate the users to use the clinical trial system 100, to authorize certain of the users to access certain trials and within these trials to access certain resources (e.g., systems or subsystems) in the clinical trial system 100, and to interconnect the constituent systems and computing devices 120, 176 and 110-118 during setup and runtime of the clinical trial via the communication network 102.

The site setup module 105 is configured to enable the trial planner 110 to setup example trial sites 114, 116, 118 (site IDs) and associate these trial sites with the clinical trial and one or more users set up via the user setup module 106.

The user setup module 106 is configured to enable the trial planner 110 to setup users who are associated with the trial planner 110, at least one shipper manager 113, trial sites 114, 116, 118, users of any other role in the clinical trial, as well as their authorizations in the clinical trial system 100. Usernames, passwords and authorizations of users in the clinical trial system 100 can be maintained by the trial administration system 104 in the user database 108.

The inventory depot setup module 109 is configured to enable the trial planner 110 to setup one or more depots 115 associated with trial sites 114-118 and shipper managers 113 in the clinical trial system 100. Each depot 115 can be associated with one or more of the trial sites and one or more of the shipper managers 113. For clarity and brevity, one depot 115 is associated with one shipper manager 113 and trial sites 114-118.

The RTSM system 120 is configured to enable the trial planner 110 to select and design randomization and treatment design for the clinical trial, as well as simulate the selected randomization design. The RTSM system 120 includes a trial administration interface 121, user interface 122, EDC interface 123, logistics interface 125, design and simulation subsystem 124, and runtime subsystem 156.

The trial administration interface 121 is configured to interconnect the trial administration system 104 with the RTSM system 120 and receives the trial ID and site IDs for the clinical trial from the trial administration system 104. Further, the user interface 122 is configured to enable the trial planner 110 to access the design and simulation subsystem 124 in order to select/configure a randomization design and treatment design associated with the clinical trial and to simulate the randomization design. The design can be simulated and configured to reduce the number of subjects necessary for the clinical trial. After the selection/configuration of the randomization design and treatment design, the user interface 122 is configured to store the received trial ID and indications of the selected/configured randomization design and treatment design in a runtime database 158 of the runtime subsystem 156.

The design and simulation subsystem 124 is configured to enable the trial planner 110 via the user interface 122 to select and configure a randomization design and treatment design for the clinical trial (trial ID) and to simulate the randomization design. The design and simulation subsystem 124 includes a randomization designer 126, randomization simulator 138, treatment designer 148, and randomization and article database 154.

The randomization designer 126 is configured to allow the trial planner 110 to configure and save a randomization design (including a plurality of randomization metrics) for the clinical trial (trial ID). FIG. 11 illustrates an example webpage generated by the randomization designer 126 to allow the configuration of a randomization design for the clinical trial. The randomization designer 126 includes an arm and arm-subject ratio module 128, randomization factor module 130, factor weight module 132, randomization-second-best-probability module 134 and strata module 136.

The arm and arm-subject ratio module 128 is configured to allow designation of arms in the clinical trial and ratio of subjects among the arms of the clinical trial. For example, if there are two arms with a ratio of 1:2, respectively, the RTSM system 120 will attempt to assign subjects to these arms such that ⅓ of the subjects are assigned to the first arm and ⅔ of the subjects are assigned to the second arm.

The randomization factor module 130 is configured to allow designation of randomizing/balancing factors for the clinical trial. For example, randomizing factors such as age, sex, metabolic rate, and/or other factors associated with the assignment of the subjects to the arms in clinical trial can be designated.

The factor weight module 132 is configured to allow designation of randomization weights for the randomizing factors designated by the randomization factor module 130.

The randomization-second-best-probability module 134 is configured to indicate a probability percentage associated with an assignment of a subject to a second-best arm, mitigating a deterministic assignment as will be described below in greater detail with reference to FIG. 7.

The strata module 136 is configured to allow designation of two or more states for each randomization factor. For example, for a randomizing factor of "sex", two states would be defined, i.e., "male" and "female". As another example, for a randomizing factor of "age", multiple states could be designated, such as, 25-35, 35-45, 45-55, 55-65 and greater than 65.

Once the randomization design has been configured using modules 128-136, the trial planner 110 can save a randomization design for the clinical trial (trial ID) via the randomization designer 126, such as via a "save" indication, to the randomization and article database 154.

The randomization simulator 138 is configured to allow the trial planner 110 simulate the saved randomization design for the clinical trial. One or more simulations can be generated, saved and executed. The simulations and their results can be saved in the randomization and article database 152. FIG. 12 illustrates an example webpage generated by the randomization simulator 138 to setup and simulate the randomization design for the clinical trial. The simulation can be used to validate that the randomization design meets the requirements of the clinical trial, including minimizing the number of subjects that are required to be enrolled in the clinical trial. The randomization simulator 138 includes a simulation setup module 140, execution module 142, result module 144, and analysis module 146.

The simulation setup module 140 is configured to receive simulation metrics from the trial planner 110 for the randomization simulations, such as, a number of simulation runs, number of subjects, number of sites and strata distribution ratios (collectively indicating a probability that a simulated subject will be generated as belonging to a stratum).

The execution module 142 is configured to execute the simulations according to the received simulation metrics. The execution module 142 generates simulation runs as indicated by the received number of simulation runs, and within each generated simulation run generates simulated subjects as indicated by the received number of subjects. Each simulated subject is generated as belonging to a trial site and strata in a probabilistic process controlled by the remaining received simulation metrics, respectively. For example, if there are two strata with distribution ratios 1:2, respectively, the process will accord a ⅓ probability of generating a simulated subject belonging to the first stratum, and ⅔ probability of generating the simulated subject as belonging to the second stratum.

Once the simulated subject is generated, the execution module 142 communicates with a randomizer 162 of FIG. 1, using algorithmic interface 160, to randomize the simulated subject to an arm in accordance with the randomization metrics of the randomization design that was configured via the randomization designer 126 described hereinabove.

Figure 13:
FIG. 13 illustrates an example webpage to display simulation results of one or more simulations executed in FIG. 12.

The result module 144 is configured to display the results of the executed simulations. The displayed results can include for each simulation executed, its simulation metrics, start time and end time, total execution time. An example simulation results webpage is shown in FIG. 13. The displayed simulation results can show for each of the runs of the simulation the distribution of the subjects across the trial arms within each of the following subject groups: (i) all the subjects in the particular run; (ii) for each site, the subjects that belong to that site; (iii) for each state of each factor, the subjects that belong to that state of that factor; (iv) for each stratum, the subjects that belong to that stratum.

The analysis module 146 is configured to aggregate and analyze the results produced by the execution module 142 for each run, and present statistically significant quantities, such as a mean, standard deviation, minimum number of subjects, and a number of times that a particular group of simulated subjects was out of balance.

The design selector 147 is configured to allow the trial planner (designer) 110 to import the design of an existing study into a new study or to link the new study to an existing study's design. The design selector 147 includes a copy design module 151 and share design module 153. The copy design module 151 provides the ability to import the design of an existing study into a new study. Changes to the design of the new study do not affect the existing study, and visa versa. The share design module 153 provides the ability to link the new study to an existing study's design so that any changes in the existing study design will affect the design of the new study, and visa versa.

Figure 15:
FIG. 15 illustrates an example webpage to configure a treatment design for a clinical trial.

The treatment designer 148 is configured to allow the trial planner 110 to configure and save a treatment design for the clinical trial (trial ID). FIGS. 15 and 16 illustrate example web pages generated by the treatment designer 148 to configure the treatment design for the clinical trial. The treatment designer 148 includes an article module 150 and arm treatment module 152.

The design reporting module 149 is configured to deliver to trial planners 110 or study managers 111 a detailed report concerning the current study design. The report enumerates and explains study arms and ratios, randomization factors and strata, randomization weights, randomization probabilities and article types and treatments. Other factors, features or aspects associated with the study design as described herein can be included in the report.

The article module 150 is configured to receive from the trial planner 110 a definition or indication of one or more article types and associated dispensation metrics for those article types. For example, "article type 1" can be defined as "Aspirin×325 mg×1 pill". As another example, "article type 2" can be "Aspirin×81 mg×1 pill". The dispensation metrics for trial sites associated with defined articles can include also indications of the minimal number of days between dispensation and expiration of the article. Additional dispensation metrics associated with the article types can be provided.

The arm treatment module 152 is configured to receive from the trial planner 110 a treatment associated with of each arm of the clinical trial. The treatment is composed by the indication of an "article type" and a "number of units" for the article type. For example, arm 1 can receive a treatment composed of 1 unit of "article type 1", arm 2 can receive 1 unit of "article type 2", while arm 3 can receive 1 unit of "article type 1" and 2 units of "article type 2".

While the foregoing examples are intended to illustrate the article module 150 and the arm treatment module 152, it should be understood that the trial planner 110 can configure various articles (different medications and dosages), as well as treatments composed of different units of these articles, via the treatment designer 148.

The randomization and article database 154 maintains the randomization design configured via the randomization designer 126, the results of the simulations generated by the randomization simulator 138, as well as the treatment design configured via the treatment designer 148.

The runtime subsystem 156 is configured to provide trial management, as well as randomization and article dispensing for subjects of the clinical trial. The runtime subsystem includes a runtime database 156, an algorithm interface 160, and a trial manager 166. The runtime database 156 maintains data for the clinical trial, including its trial ID, site IDs, randomization design, treatment design, as well as live data including subject records, inventory item and batch records, and shipment records for the clinical trial.

The EDC interface 123 is configured to interface with one or more different trial EDCs to receive requests to assign (randomize) subjects to the arms of the clinical trial and to indicate a set of units of articles types to dispense to the subjects. The EDC interface 123 interfaces with an algorithm interface 160 that includes a randomizer 162 and an article dispenser 164, which assign the subjects to the arms of the clinical trial and identify the units if article types, respectively. The algorithm interface 160 also includes a shipping (shipper) algorithm 165. The EDC interface 123 returns the subject assignments and unit identifications to the requesting trial EDCs.

The randomizer 162 is configured to receive randomization data (e.g., trial ID, site ID, subject ID, and state of the subject ID in each of the factors defined in the randomization design) from a randomization custom function (CF) 186 of the trial EDC 176, as will be described greater detail below with reference to the trial EDC 176. As described hereinabove, the randomizer 162 is also configured to receive simulated randomization data (e.g., simulated trial ID, site ID, subject ID, and state of the subject ID in each of the factors defined in the randomization design) from the randomization simulator 138.

The randomizer 162 is further configured to retrieve the randomization design for the trial ID. In one embodiment, the randomizer 162 retrieves an indication of the randomization design associated with the trial ID from the runtime database 158 and further retrieves the randomization design from the randomization and article database 154 based on the indication. In another embodiment, the randomizer 162 is configured to retrieve the randomization design for the simulated trial ID from the randomization and article database 154.

The randomizer 162 is also configured to assign (randomize) the subject (subject ID) to an arm (arm ID) of the clinical trial (trial ID) based on the randomization design, as well as to store the trial ID, site ID, subject ID, states of the factors, and arm ID assignment to the runtime database 158. Subject assignment to the arm of the clinical trial is described in greater detail below with reference to FIG. 7. The randomizer 162 is further configured to transmit a randomization indicator to the randomization CF 186 of the trial EDC 176, which indicates that the subject has been assigned (randomized) in the clinical trial. For simulations, the randomizer 162 is similarly configured to store simulated data and assignments to the randomization and article database 154 and to return a randomization indicator to the randomization simulator 138.

The article dispenser 164 is configured to receive article dispense data (e.g., trial ID, site ID, subject ID, and visit ID) from a dispense CF 188 of the trial EDC 176, as will be described greater detail below with reference to the trial EDC 176. The article dispenser 164 is further configured to retrieve an arm ID for the subject ID from the runtime database 158, which indicates to which arm the subject ID is assigned. The article dispenser 164 is further configured to determine a treatment (e.g., set of one or more units of articles) for the arm ID from the treatment design associated with the clinical trial ID in the randomization and article database 154. Further, the article dispenser 164 is configured to determine whether there are sufficient units of articles in the inventory associated with the trial ID that comply with dispensation metrics for the site ID. If so, the article dispenser 164 transmits a set of units of the articles to the dispense CF 188 of the trial EDC 176 for dispensing to the subject ID. The article dispenser 164 is also configured to adjust the inventory for the trial ID based on the dispensed set of units to the subject ID.

The logistics interface 125 interfaces the study managers 111 and supply managers 112 with algorithm interface 160. More specifically, the logistics interface 125 allows study managers 111 and supply managers 112 to set "supply plans" for trial sites 114-118.

A supply plan determines the triggers and supply levels that the shipper algorithm 165 will aim to maintain for the trial sites (e.g., trial sites 114-118) that are assigned to that supply plan. Different supply plans can be defined for different trial sites. A supply plan defines how trial sites associated with that supply plan will be supplied. Each supply plan defines: (i) a unique name; (ii) four parameters for each article type, (a) minimal number of days between shipping and expiration, (b) initial site stocking level, (c) resupply threshold level, and (d) resupply stocking level; and (iii) a parameter that sets the supply plan as the default for the study.

As will be described in greater detail with reference to FIG. 22, the logistics interface 125 provides several user interface screens to manage supply plans: (i) the supply plan list interface; and (2) the supply plan manage interface. The supply plan manage interface illustrates the details of a specific supply plan and is used for adding, changing and deleting supply plans. The supply plan list interface shows the list of supply plans.

The shipping algorithm 165 is executed periodically or upon request. In some embodiments, the shipment module 172 via algorithm interface 160 can periodically (e.g., every night) execute the shipping algorithm 165. Alternatively or in addition, shipper managers 113, study managers 111 and supply managers 112 can also manually execute the shipping algorithm 165 from the shipments user interface (e.g., FIG. 19), such as via the logistics interface 125.

When the shipping algorithm 165 is executed, for every trial site and every article type, it compares the number of items of that article type that are either available at trial site (let a1 be the number of such items), or are currently being shipped to that site (let a2 be the number of such items) or allocated to be shipped to that trial site (let a3 be the number of such items), with the threshold number for that article type (let t be the number of such items) as defined in the trial site's supply plan.

Accordingly, if $a1+a2+a3 \leq t$, the shipping algorithm 165 will allocate new items of that article type that are available for shipping at the trial site's associated depot 115 to a new shipment. Where r is the resupply target set for that article type in the trial site's supply plan, the shipping algorithm 165 will allocate $r-(a1+a2+a3)$ items for shipment. It should be noted that the shipping algorithm 165 will only allocate to a trial site items that have an expiry date later than the "minimal number of days between shipping and expiry" value set in that trial site's supply plan. The shipping algorithm 165 will also prefer to ship items with sooner expiry days rather than later ones, as long as the items satisfy the restrictions above.

The shipping algorithm 165 will traverse through all the article types, and once done, all the items allocated for shipment for the specific trial site will be collected into a new shipment record. The shipping algorithm 165 can then issue (and transmit) an email to the supply managers 112, as well as any shipper manager 113 associated with a depot 115 (associated with the trial site), alerting them to the existence of a new pending shipment (shipment record).

By following a link provided in such email, a shipper manager 113 associated with the depot 115 can access the shipment record, review the list of items requested for shipping, ship those items, and then confirm the shipment. The shipper manager 113 can also dissolve the shipment, resetting the status of the items in the shipment to "available for shipment" once again. It should be noted that dissolving a shipment assigns the inventory items in that shipment to an "available for shipment" status at the depot 115 with which their batch is currently associated. For example, if a request for shipment s is created for depot d1, inventory item i is included in this shipment and item i belongs to batch b (this can only happen if b is assigned to depot d1 as well). In this example, assume that after the shipment request s is created, batch b is reassigned to depot d2 Thus, if shipment s is dissolved, item i is marked as "available for shipping" at depot d2.

Moreover, the shipping algorithm 165 is also configured to issue email notifications for shipments that have been requested as well as when depots 115 run out of stock.

The trial manager 166, which can be accessed via user interface 122, is configured to provide management functionality for the different users of the clinical trial system 100, such as of the trial planner 110, study manager 111, supply manager 112 and shipper manager 113, and personnel from trial sites 114-118. The trial manager 166 includes a site module 168, subject module 170, shipment module 172, and inventory module 174.

While the trial planner 110 generally configures the trial sites via site setup 105 of the trial administration system 104, and configures depots 115 via inventory depot setup 109, the site module 168 is configured to enable the study manager 111 to manage RTSM parameters associated with each of the trial sites in the clinical trial. FIG. 17 illustrates an example webpage generated by the site module 168 for the clinical trial, including one or more trial sites (e.g., trial sites 1114, 116, 118). For each trial site, site module 168 is configured to allow setup of a supply plan and assignment of a depot (e.g., depot 115) for the trial site, as well as to present a number (site ID), number of subjects randomized to the trial site, number of shipments to the trial site and number of inventory items at the trial site. The site module 168 is further configured to enable the study manager 111 to activate/deactivate drug shipping from the depot (e.g., depot 115) to each of the trial sites (e.g., trial sites 114-118).

In addition, supply plans play an important role in the site module 168. The site module 168 is configured to assign and provide for each site the supply plan it is associated with and can assign trial sites to a supply plan "en mass".

The subject module 170 is configured to enable the study manager 111 and trial sites 114-118 to manage the subjects in the clinical trial. FIG. 18 illustrates an example webpage generated by the subject module 170 for the clinical trial, including one or more subjects (subject IDs). In one embodiment, for each subject ID, the subject module 170 is configured to provide stratum, trial site (site ID), trial arm (arm ID), arm selection method and when the subject was assigned (randomized) to the trial arm. The actual data of the clinical trial that is displayed by the subject module 170 to various users depends on their authorizations (or permissions) provided by the user setup module 106 of the trial administration system 104.

Importantly, these permissions determine the scope of the user access to the subject population in the clinical trial. For example, the study manager 111 could view a list of subjects enrolled in multiple trial sites, whereas trial site 114 could only view subjects belonging to that trial site. Furthermore, different users can have different display for the same subjects. For example, the study manager 111 may have access to view arm assignments of subjects, while other users, such as trial sites 114-118, may not have such access to arm assignments.

The design update module 171 is configured to enable the trial planner (designer) 110 to modify or update the study design at runtime, i.e., after the study has already gone live. The design update module allows modification the ratios of study arms via the arm ratios module 128, weights of the randomization factors via the factor weight module 132, probability percentage via the randomization probability module 134, and minimal time between dispensation and expiry via the article module 150.

The shipment module 172 is configured to enable the supply manager 112, trial sites 114-118, as well as shipper manager 113 to manage the article shipments in the clinical trial. FIG. 19 illustrates an example webpage generated by the shipment module 172 for the clinical trial, including one or more shipments. Each of the one or more shipments can include a name of the shipment, trial site (site ID), date shipment was shipped from depot by shipper manger, date the shipment was received at the trial site, a tracking number associated with the shipment, and units of articles shipped in the shipment. The shipment module 172 includes "waste and replace" functionality configured to allow the shipper manager 113 to mark items reserved for the shipment as wasted, and request replacements for inclusion in the shipment. Permissions of the users configured via the trial administration system 104 also affect the data displayed by the shipment module. The permissions determine the scope of user access to the shipments in the clinical trial. For example, trial site 114 will be able to see shipments destined for trial site 114, but will not be able to see shipments destined for trial site 116. Similarly, the shipper manager 113 can see just those shipments originating from a depot 115 with which the shipper manager 113 is associated, and not shipments originating from others depots (not shown).

The unblinding module 173 is configured to authorize subject unblinding or item unblinding for subjects or items, respectively. In most clinical trials subjects remain "blinded", e.g., without disclosure to which study arm subject were randomized, and to which article types inventory items belong. The unblinding module 173 allows authorized users to get access to this information. This action can be audited by the audit module 169 as described below.

The audit module 169 is configured to allows the study manager 111 to audit or view any changes that were made to the study design, to the supply plans, to the site's associated depots or supply plans as well as any changes that happened to any subject, inventory item, inventory batch or shipment record.

The inventory module 174 is configured to enable the trial planner 110, study manager 111, shipper manager 113, and trial sites 114-118 to manage the inventory associated with the clinical trial. FIGS. 19 and 20 illustrate example web pages generated by the inventory module 174 for the clinical trial. For example, FIG. 19 illustrates a general inventory item list, while FIG. 20 illustrates a list of batched items uploaded by the inventory module 174 via user interface 122, from the trial manager 111 or shipper manager 113, into the clinical trial inventory in the runtime database 158. Again, permissions of users determine the scope over the list of items available and information available for each item to the users.

The EDC system 176 is configured to receive and maintain data associated with a clinical trial from the trial sites 114, 116, 118 and the RTSM 120. The EDC system 176 can be any clinical trial data capture system that can execute a custom function described herein to communicate with the RTSM system 120. The EDC 176 includes trial database 178, trial setup subsystem 180 and trial runtime subsystem 182. These subsystems of the EDC system 176 are not exhaustive, but are meant to illustrate the integration of the RTSM system 120 and EDC system 176, which is described in this application. Accordingly, one or more additional subsystems or components can be included in a particular EDC system 176.

The trial database 178 maintains data associated with the clinical trial, such as subjects, trial sites and dispensed units of articles, as well as clinical information collected for the subjects during the clinical trial. The trial setup subsystem 180 is configured to receive a trial ID and site ID associated with the clinical trial from the trial administration system 104, when a trial site (e.g., trial site 114) logs into the trial administration system 104. The trial setup subsystem 180 is further configured to store and maintain the received trial ID, site ID and associated trial data in the trial database 178.

The trial runtime subsystem 182 is configured to receive data of a subject from a trial site (e.g., trial site 114) and to enroll the subject into the clinical trial. It is to be noted that multiple subjects can be enrolled from each of the trial sites 114, 116, 118. The trial runtime subsystem 182 is further configured to randomize the enrolled subjects in the clinical trial and to dispense appropriate medication to the subjects via the RTSM system 120. The trial runtime subsystem 182 includes a subject data input module 184, randomization CF 186, and dispense CF 188.

The subject data input module 184 is configured to receive data associated with a subject to be enrolled into the clinical trial, for example, from trial site 114. This data can include the subject's enrollment consent form and personal data associated with the subject (e.g., name and contact information). The received data also includes states of the subject in each of the one or more factors required for randomization of the subject in the clinical trial, as described hereinabove with reference to the randomizer 162 of the RTSM 120. It should be noted that the states of the factors can also be received by the subject data input module 184 via integration of the EDC system 176 with other clinical information systems that collect subject information at the start or during the clinical trial. The subject data input module 184 is further configured to assign the enrolled subject a subject ID and to add a new subject record for the subject ID to the trial database, which includes the trial ID, site ID, states of the factors and any other information received for the subject from the trial site (e.g., trial site 114).

The randomization CF 186 is configured to randomize a subject ID. Specifically, the randomization CF 186 determines whether randomization of the enrolled subject (subject ID) has been triggered via input received by the subject data input module 184. The randomization trigger can be automatically determined based on whether all required input for randomization has been received for the subject ID (e.g., from trial site 114) or can be user-initiated from the trial site (e.g., trial site 114). Once triggered, the randomization CF 186 is configured to convert the trial ID, site ID, subject ID and the states of the subject in the factors to RTSM randomization data. The randomization CF 186 is further configured to transmit the RTSM randomization data to the EDC interface 123 of RTSM system 120 and to receive a randomization indicator that indicates successful assignment (randomization) of the subject ID to an arm of the clinical trial. The randomization CF 186 stores the randomization indicator to the record of the subject ID in the trial database 178.

The dispense CF 188 is configured to determine the number of units of articles to dispense to the subject ID at a visit to the trial site (e.g., trial site 114). The visit can be at the same time the subject ID is enrolled and randomized in the clinical trial and/or a later visit, being indicated by a visit ID. The visit ID can be any alphanumeric string that uniquely identifies the dispensing (e.g., a date indicator). The dispense CF 188 determines whether dispensing to the subject ID has been triggered by the trial site (e.g., trial site 114), such as via user-initiated input. Once triggered, the dispense CF 188 adds a dispense record for the subject's record associated with the subject ID, which includes a dispense indication. The dispense CF 188 is configured to convert the trial ID, site ID, subject ID visit ID to RTSM dispense data. The dispense CF 188 is further configured to transmit the RTSM dispense data to the EDC interface 123 of RTSM system 120 and to receive a set of one or more units indicators to be dispensed to the subject ID. The dispense CF 188 stores the dispense unit indicators to the visit record of the subject ID in the trial database 178.

Figure 2:
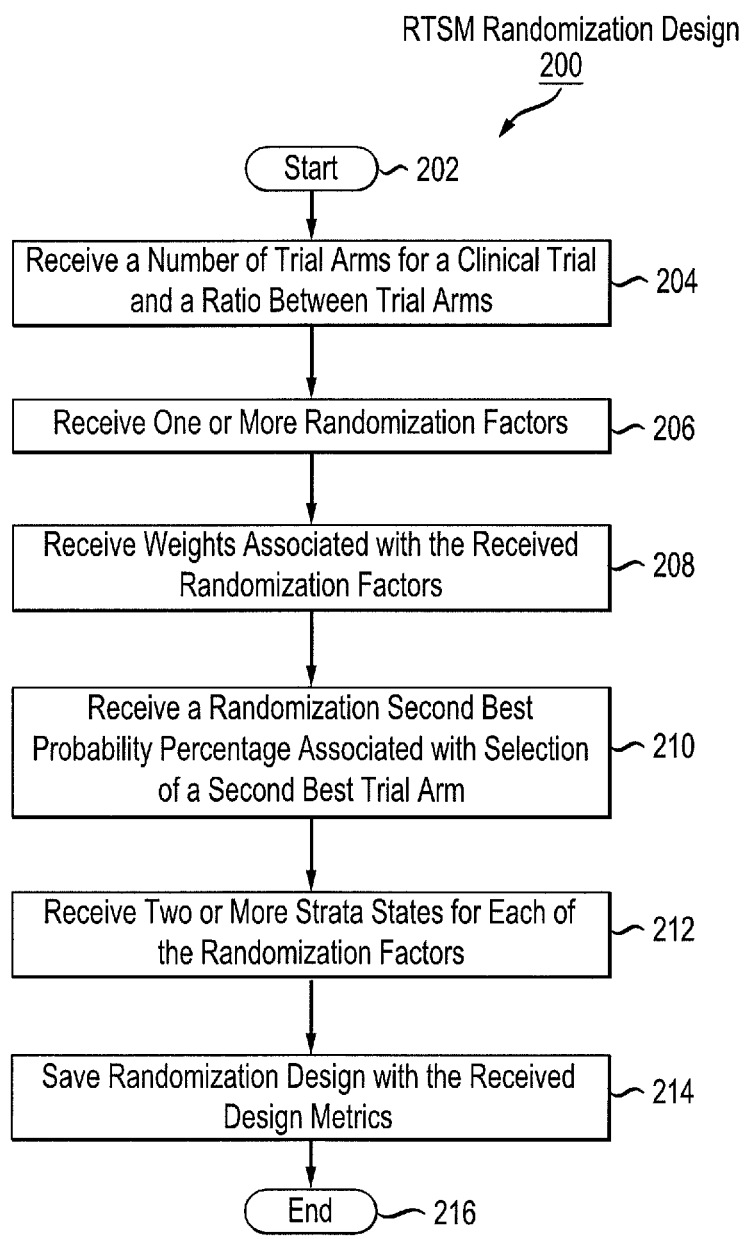
FIG. 2 illustrates a flowchart of an example method of configuring a randomization design for a clinical trial.

FIG. 2 illustrates a flowchart of an example method 200 for configuring a randomization design for a clinical trial. The method 200 starts at operation 202 where the trial planner 110 invokes or executes the randomization designer 126 to configure the randomization design, as illustrated in FIG. 1. At operation 204, a number of trial arms are received for a clinical trial. Zero or more randomizing factors, such as age, sex and/or one or more other factors are received at operation 206. At operation 208, weights associated with clinical trial, trial site and strata, as well as with the randomization factors of operation 206 are received. At operation 210, a second best probability percentage associated with the randomization of subjects is received. Two or more strata states are received at operation 212 for each of the randomization factors received at operation 206. At operation 214, the randomization design with the received design metrics is saved, for example, in the randomization and article database 154.

Figure 3:
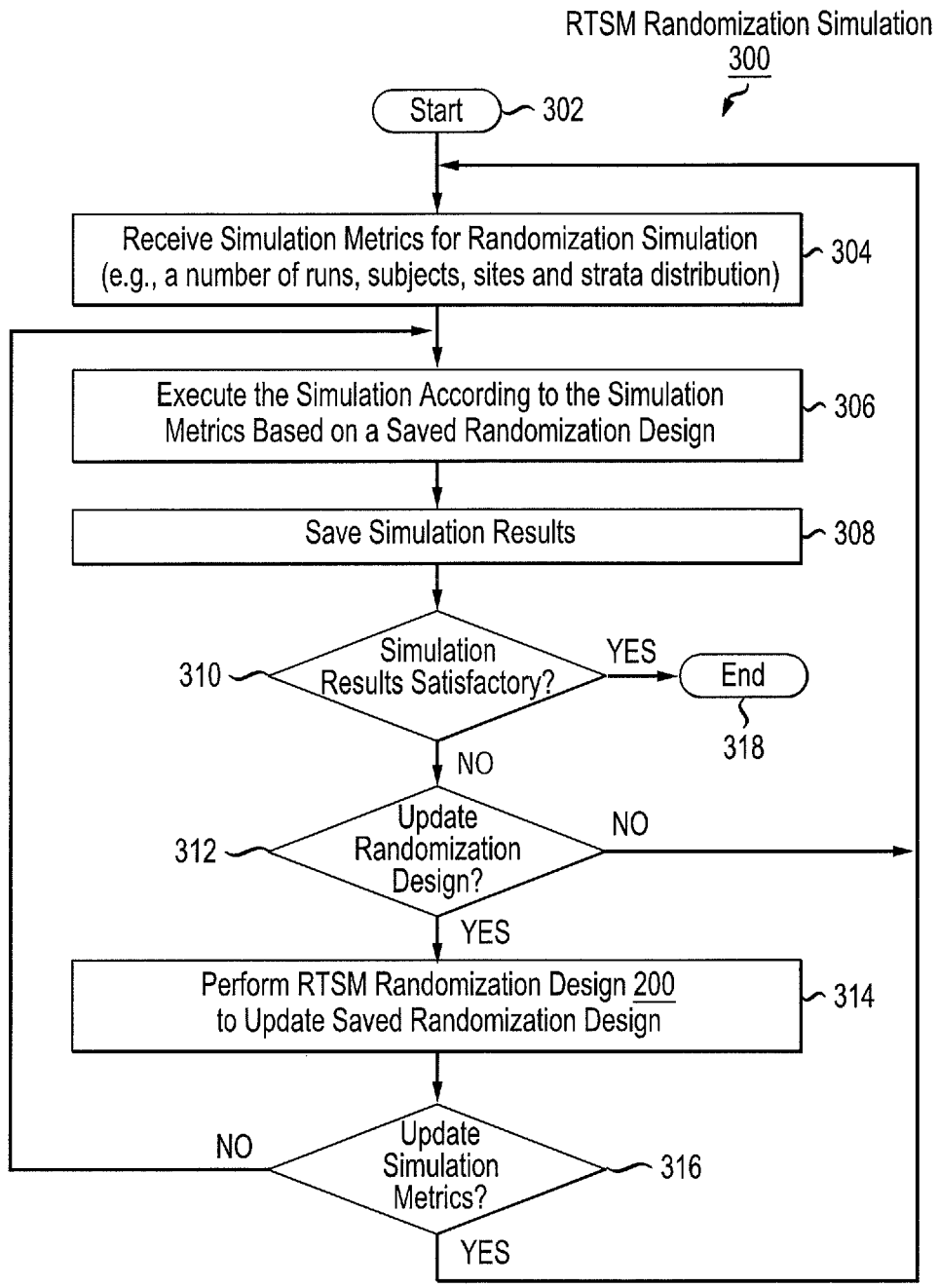
FIG. 3 illustrates a flowchart of an example method of performing a randomization simulation of a randomization design generated in accordance with FIG. 2.

FIG. 3 illustrates a flowchart of an example method 300 for performing a randomization simulation of a randomization design generated in accordance with FIG. 2. The method 300 starts at operation 302 where the trial planner 110 invokes or executes the randomization simulator 138 to perform the randomization simulation, as illustrated in FIG. 1. At operation 304, simulation metrics for the randomization simulation are received. The simulation metrics can include number of execution runs, subjects and trial sites, as well as strata distribution. At operation 306, the randomization simulation is executed according to the received simulation metrics based on the randomization design generated in FIG. 2. At operation 308, the simulation results of the simulation are saved, such as in the randomization and article database 152 illustrated in FIG. 1.

At operation 310, a determination is made as to whether the randomization simulation yielded satisfactory results for the randomization design. The reasons for determining that the whether the simulation results are satisfactory can include, but are not limited to, high frequency of imbalance among runs at one or more group of subjects (e.g., group of subjects in the entire clinical trial, groups of subjects at trial sites, groups for states of subject factors, and groups for subject strata), too few or too many subjects assigned to at least one arm within one or more of the groups, or too high variability among the runs.

If it is determined that the simulation results were satisfactory at operation 310, the method ends at operation 318. However, if it is determined that the simulation results were not satisfactory at operation 310, the method 300 continues at operation 312, where a determination is made as to whether the randomization design should be updated. If it is determined that the randomization design should not be updated at operation 312, the method continues at operation 304 to receive updated simulation metrics for the randomization simulation, and the simulation is executed according to the updated simulation metrics and the previously saved randomization design at operation 306.

If it is determined that the randomization design should be updated at operation 312, the method continues at operation 314 to invoke method 200 of FIG. 2 for updating the randomization design (design metrics of the randomization design). At operation 316, a determination is made whether simulation metrics for the randomization simulation should be updated.

If it is determined that simulation metrics should be updated at operation 316, the method 300 continues at operation 304 to receive simulation metrics for the randomization simulation. At operation 306, the simulation is executed according to the updated simulation metrics and the updated randomization design.

However, if it is determined that simulation metrics should not be updated at operation 316, the method continues at operation 306 to execute the randomization simulation according to the previously received simulation metrics and the updated randomization design.

Figure 4:
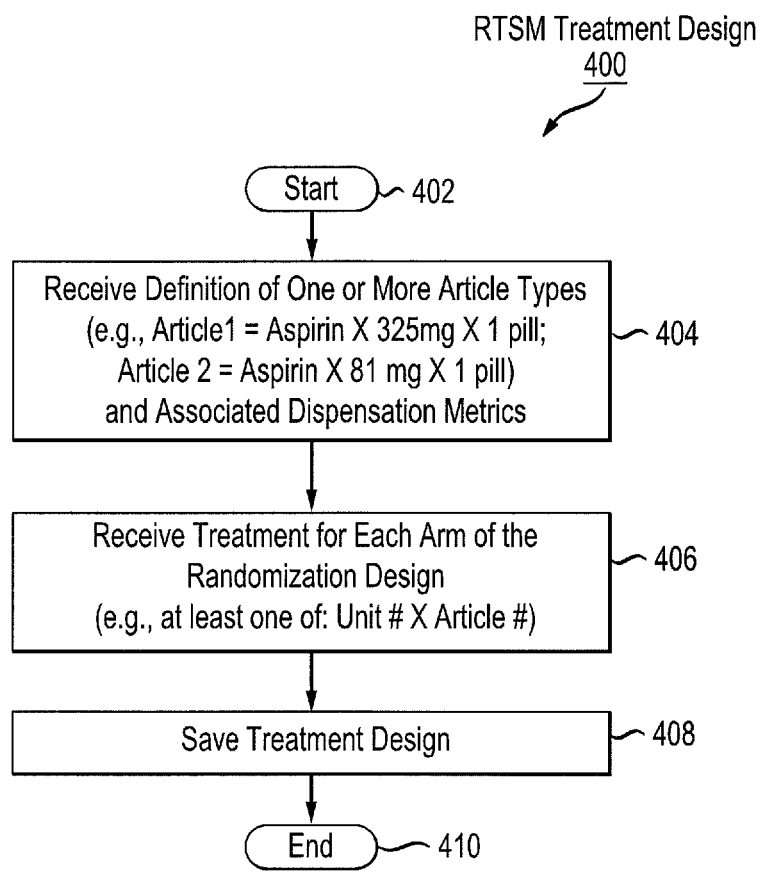
FIG. 4 illustrates a flowchart of an example method of configuring a treatment design for a clinical trial.

FIG. 4 illustrates a flowchart of an example method 400 for configuring a treatment design for a clinical trial. The method 400 starts at operation 402 where the trial planner 110 invokes or executes the treatment designer 148 to configure the treatment design, as illustrated in FIG. 1.

At operation 404, definitions of one or more article types and associated dispensation metrics are received for the clinical trial. For example, "article type 1" can be defined as "Aspirin×325 mg×1 pill" and "article type 2" can be "Aspirin×81 mg×1 pill". The article type indicates the medication, dosage, and pill count number. A treatment associated with each arm of the clinical trial is received at operation 406. The treatment is composed by the indication of an "article type" and a "number of units" for the article type. For example, arm 1 can receive a treatment composed of 1 unit of "article type 1", arm 2 can receive 1 unit of "article type 2", while arm 3 can receive 1 unit of "article type 1" and 2 units of "article type 2".

At operation 408, the treatment design is saved, such as in the randomization and article database 152 illustrated in FIG. 1. Thereafter, the method 400 ends at operation 410.

Figure 5:
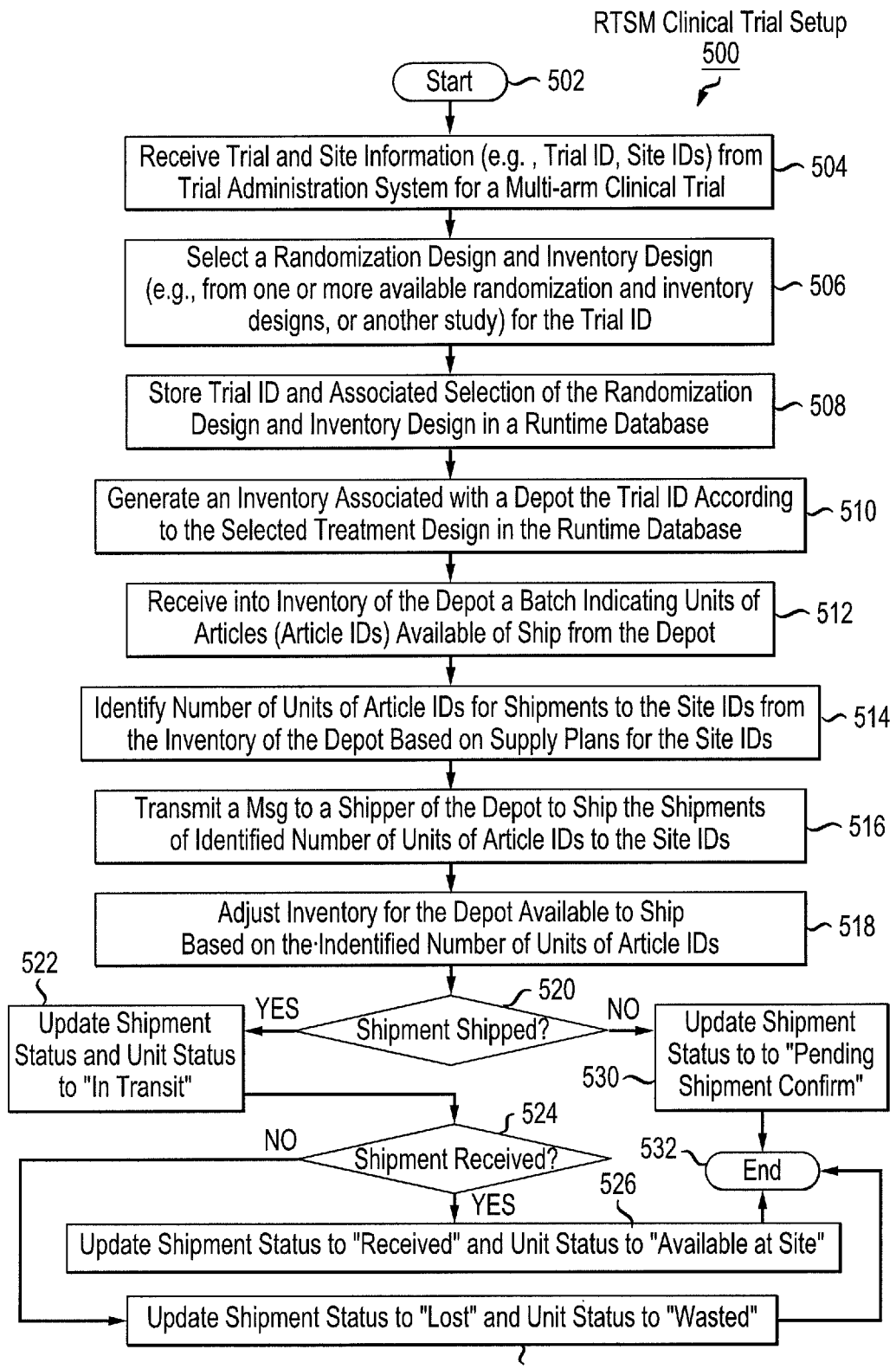
FIG. 5 illustrates a flowchart of an example method for setting up a clinical trial via a trial administration interface of an RTSM system of FIG. 1.

FIG. 5 illustrates a flowchart of an example method 500 for setting up a clinical trial via the trial administration interface 122 of the RTSM system 100 of FIG. 1. The method 500 starts at operation 502 where the trial planner 110 logs into the trial administration system 104. At operation 504, trial and site information associated with clinical trial are received from the trial administration system 104. The received information can include a trial ID that identifies the clinical trial and site IDs associated with the trial ID that identify the trial sites of the clinical trial.

At operation 506, a randomization design and treatment design are selected for the clinical trial (trial ID) from one or more saved randomization designs and treatment designs. The trial ID and associated selection of the randomization and treatment design are stored, such as in the runtime database 158 of the runtime subsystem 158, as operation 508. At operation 510, an inventory associated with a depot 115 is generated for the trial ID according to the selected treatment design, such as in the runtime database 158. An inventory batch that indicates units of articles (article IDs) that are available to ship by the depot 115 are received into the inventory of the depot at operation 512.

At operation 514, a number of units (unit IDs) of articles (article IDs) for shipment to the site IDs are identified from the inventory of the depot 115 based on supply plans associated with the site IDs. A message is generated and transmitted to the shipper manager 113 of the depot 115 to ship one or more shipments of identified unit IDs of Article IDs to the site IDs at operation 516. At operation 518, the inventory for the depot 115 is adjusted to reflect articles available to ship from the depot 115 based on the identified unit IDs of Article IDs.

At operation 520, a determination is made as to whether the shipments have been shipped to the trial sites. Initially, shipment status of a shipment is "requested". When a shipment is shipped by the shipper manager 113 from the depot 115, the inventory is updated to reflect shipment status and unit status to "in transit". The shipper manager 113 can also "dissolve" the shipment such that the shipment is marked as "dissolved" and items collected for shipment are marked as "available at depot". At operation 524, a further determination is made as to whether the shipment has been received. If it is determined that the shipment was received, then the shipment status is updated to "received" and unit status is updated to "available at site". If it is determined that the shipment was not received, then the shipment status is updated to "lost" and unit status is updated to "wasted". Thereafter, the method 500 ends at operation 532.

If it is determined that the shipment was not shipped at operation 520, then at operation 530, the shipment status is updated to "pending shipment confirm". Thereafter, the method 500 ends at operation 532.

Figure 6:
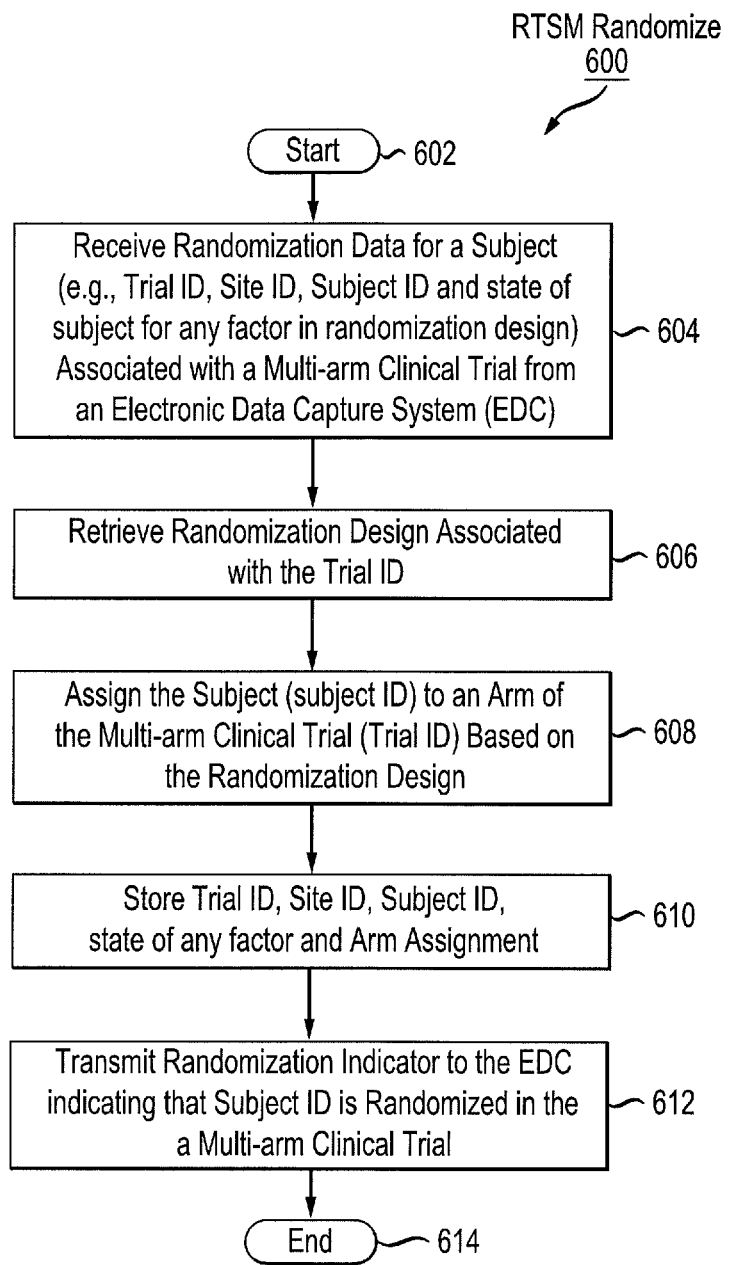
FIG. 6 illustrates a flowchart of an example method of randomizing a subject via a randomizer illustrated in FIG. 1.

FIG. 6 illustrates a flowchart of an example method 600 for randomizing a subject via randomizer 162 illustrated in FIG. 1. The method 600 starts at operation 602 where the EDC 176 has enrolled a subject (subject ID) provided by a trial site (site ID), for example trial site 114, into a clinical trial (trial ID). At operation 604, randomization data is received for a subject from the randomization CF 186 of the EDC 176. The randomization data includes trial ID, site ID, subject ID, and state of the subject for factors identified in the randomization design. At operation 606, the randomization design associated with the trial ID is retrieved, such as from the randomization and article database 154.

At operation 608, the subject (subject ID) is assigned to an arm (arm ID) of the clinical trial (trial ID) based on the randomization design. An example method of assigning (randomizing) the subject to the arm of the clinical trial is described in detail below with reference to FIG. 7. More specifically, the randomization design is executed to assign the subject ID to the arm ID of the trial ID. The trial ID, site ID, subject ID, arm ID, and states of factors are stored, such as in the runtime database 158, at operation 610. Thereafter, at operation 612, a randomization indicator that indicates assignment of the subject (subject ID) is transmitted to the randomization CF 186 of the EDC 176. The method 600 ends at operation 614.

Figure 7:
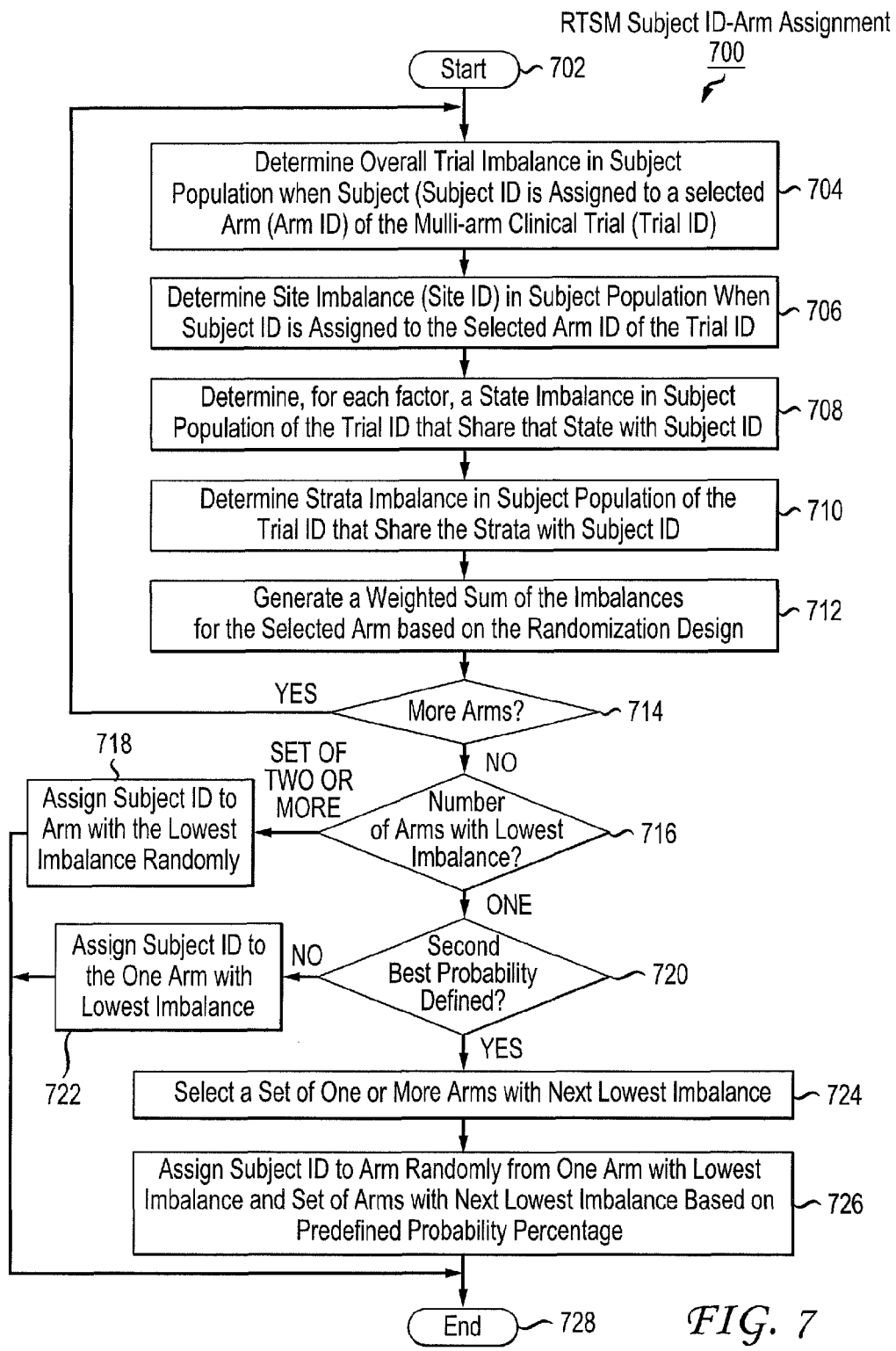
FIG. 7 illustrates a flowchart of an example method of assigning a subject to an arm of a clinical trial.

FIG. 7 illustrates a flowchart of an example method 700 for assigning a subject to an arm of a clinical trial. The example method 700 can be performed by the randomizer 162 illustrated in FIG. 1. The method 700 starts at operation 702 in which trial ID, site ID and subject ID are provided from operation 608 of FIG. 6.

At operation 704, an overall trial imbalance in subject population is determined when the subject ID is treated hypothetically as if assigned to a selected arm (Arm ID) of the trial ID. A site imbalance is determined for the site (site ID) in the subject population when the subject ID is assigned to the selected arm ID of the trial ID at operation 706. At operation 708, a state imbalance is determined for each factor in the subject population of the trial ID that shares that state with the subject ID. At operation 710, strata imbalance is determined in subject population that share the strata with subject ID.

Thereafter, at operation 712, a weighted sum of the imbalances for the selected arm (arm ID) is generated based on the randomization design. The weighted sum is saved temporarily for the selected arm ID. At operation 714, a determination is made as to whether there are additional arms to process. If it is determined that there are additional arms, then the method 700 performs operations 707-714 for the remaining arm IDs, saving temporarily the weighted sum of the imbalances for every processed arm ID.

If it is determined that there are no additional arms to process at operation 714, then the method 700 continues at operation 716, where a determination is made as to whether there is a set of two or more arm IDs having the lowest weighted sum. If it is determined there are multiple arms with the lowest weighted sum at operation 716, then the subject ID is assigned randomly to an arm ID among the set of arm ID at operation 718. Thereafter, the method 700 ends at operation 728.

However, if it is determined there is one arm with the lowest weighted sum at operation 716 then the method continues at operation 720, where a determination is made as to whether a second best probability percentage has been defined or set in the randomization design for the clinical trial. If the second best probability percentage has not been set at operation 720, then the subject ID is assigned to the arm ID with the lowest weighted imbalance determined at operation 716.

Alternatively, if the second best probability percentage has been set at operation 720, the method 700 continues at operation 724, where a set of one or more arms (arm IDs) having a next lowest weighted imbalance is selected. At operation 726, the subject ID is assigned to an arm randomly from the one arm with the lowest weighted imbalance and the set of arms with the next lowest weighted imbalance based the second best probability percentage. For example, if the second best probability percentage is set to 10%, the one arm with the lowest weighted imbalance will be selected randomly 90% of the time, while an arm in the set with next lowest weighted imbalance will be selected randomly 10% of the time.

Figure 8:
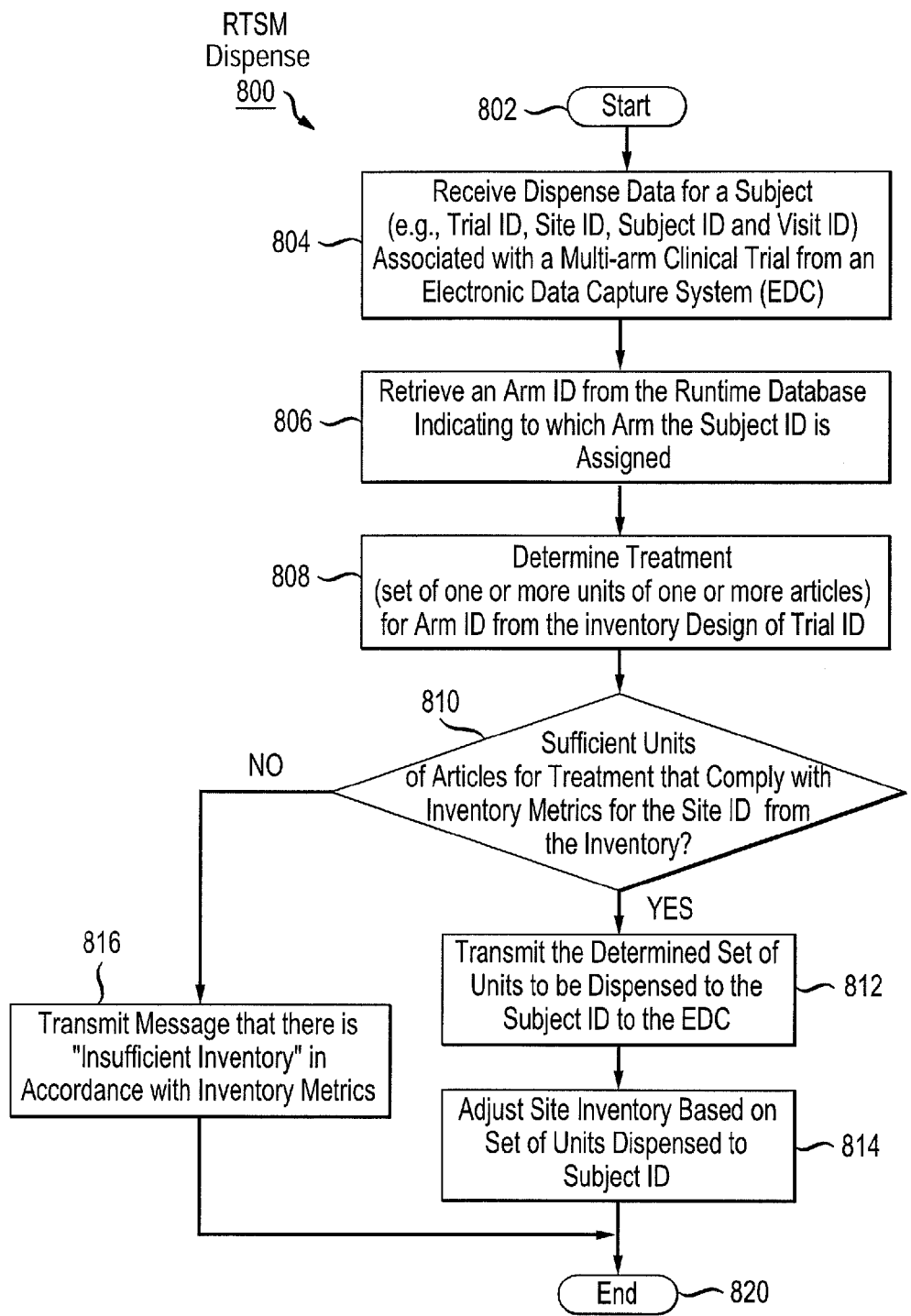
FIG. 8 illustrates a flowchart of an example method of dispensing medication via article dispenser 164 illustrated in FIG. 1.

FIG. 8 illustrates a flowchart of an example method 800 for dispensing via article dispenser 164 illustrated in FIG. 1. The method 800 starts at operation 802 where the EDC 176 has enrolled a subject (subject ID) provided by a trial site (site ID) into a clinical trial (trial ID) and has randomized the subject ID into an arm (arm ID) of the trial ID via randomizer 162 of FIG. 1. At operation 804, dispense data is received for a subject from the dispense CF 188 of the EDC 176. The dispense data includes trial ID, site ID, subject ID, and visit ID associated with the clinical trial.

At operation 806, an arm (arm ID) is retrieved for the subject (subject ID) from the runtime database 158 indicating to which arm the subject is assigned. At operation 808, a treatment (set of one or more units of one or more articles) is determined for the arm ID from the treatment design for the clinical trial (Trial ID). At operation 810, a determination is made as to whether there are sufficient units of articles at the site ID for a treatment that complies with dispensation metrics for the site ID from the inventory in runtime database 158.

If it is determined that there are sufficient units, the set of units to be dispensed to the subject ID is transmitted to the dispense CF 188 of the EDC 176. The trial site can dispense the identified units of articles to the subject indicated by the subject ID. At operation 814, inventory for the site ID is adjusted based on units dispensed to the subject ID. The method 800 ends at operation 820.

However, if it is determined that there are insufficient units, a message of "insufficient inventory" is transmitted to the dispense CF 188 of the EDC 176 at operation 818. The trial site can then notify the trial planner 110 or the shipper manger 113 of a depot concerning the inventory at the trial site. Other mitigation procedures may be invoked if there is a determination of inventory insufficiency at a trial site. The method 800 ends at operation 820.

Figure 9:
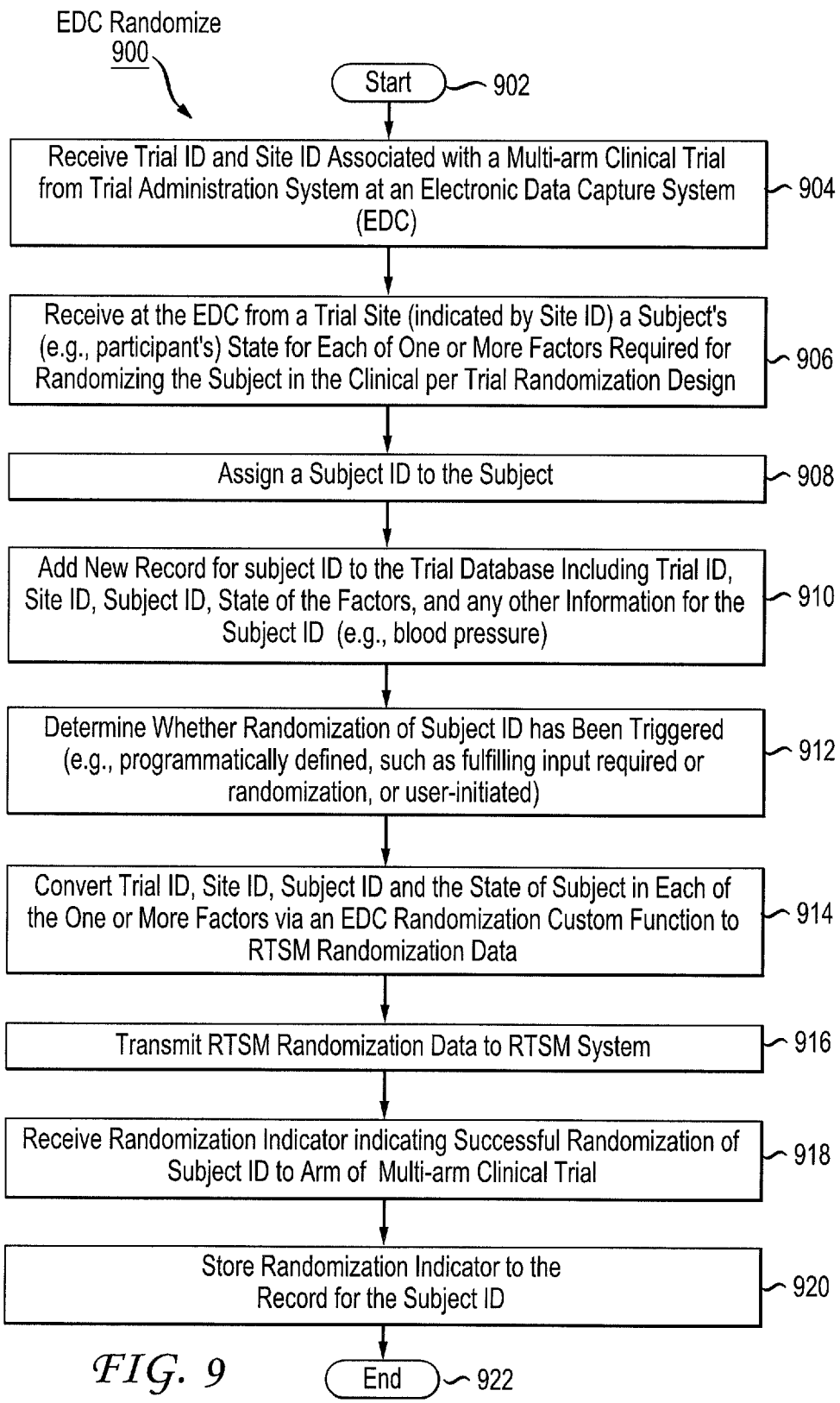
FIG. 9 illustrates a flowchart of an example method of randomizing a subject via a trial EDC system illustrated in FIG. 1.

FIG. 9 illustrates a flowchart of an example method 900 for randomizing a subject via the trial EDC 176 illustrated in FIG. 1. The method 900 starts at operation 602 where a trial site (e.g., trial site 114) has logged on via the trial administration system 104. At operation 904, a trial ID and a site ID are received from the trial administration system 104 for the logged on trial site. At operation 906, the subject's states for factors required to randomize the subject in the clinical trial (per randomization design) are received from the trial site (e.g., trial site 114). Other information concerning the subject can also be received (e.g., name, contact information, as well as other information for the clinical trial).

At operation 908, the subject is assigned a subject ID. A new record for the subject ID is added to the trial database 178. The record can include trial ID, site ID, states of the factors, as well as any other information associated with the subject (subject ID).

At operation 912, it is determined whether randomization of the subject ID has been triggered, such as programmatically when certain input requirements for randomization are fulfilled or when randomization is user-initiated. If not trigged, the method 900 waits until a trigger is received. Once randomization is triggered at operation 914, the trial ID, site ID, subject ID and states of the factors are converted via randomization CF 186 to RTSM randomization data.

At operation 916, the RTSM randomization data is transmitted to the randomizer 162 of the RTSM system 120. A randomization indicator that indicates successful randomization is received from the randomizer 162 at operation 918.

The randomization indicator is stored to the record for the subject ID at operation 920. The method 900 ends at operation 922.

Figure 10:
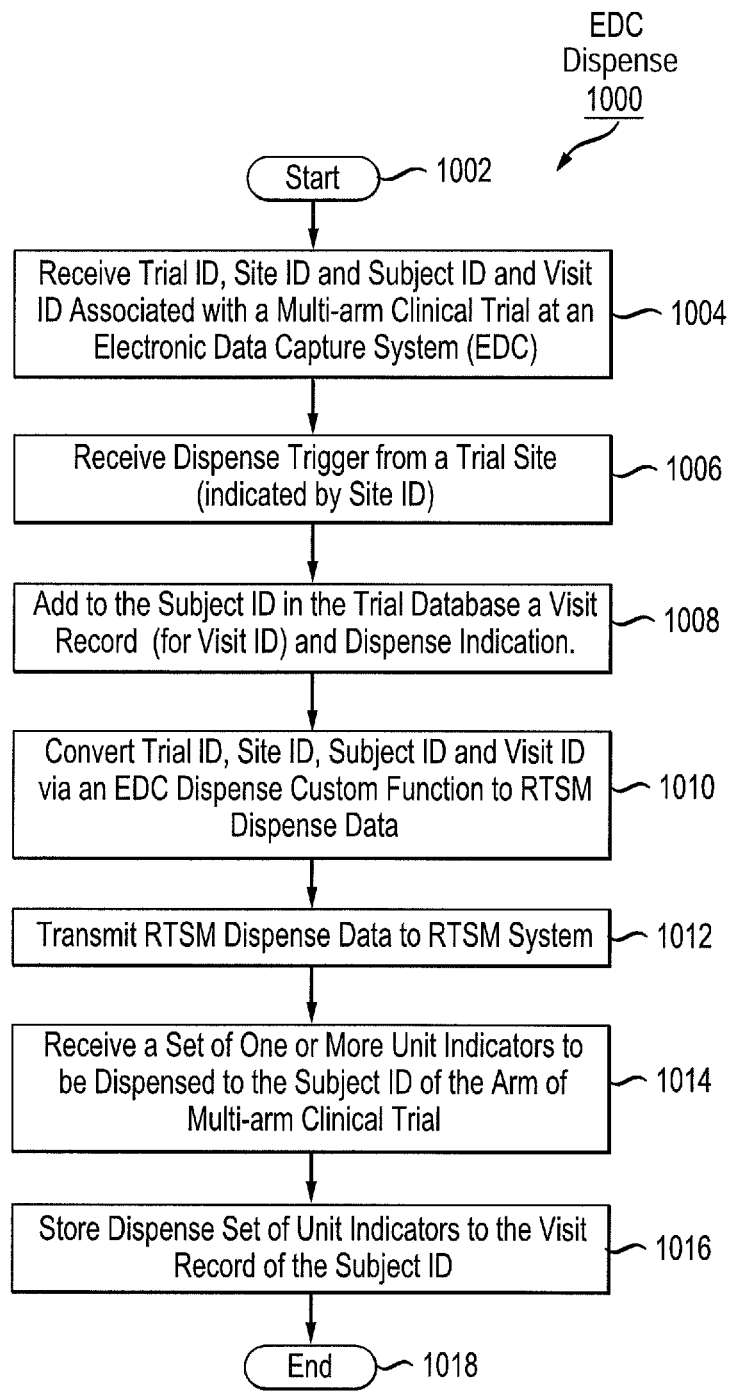
FIG. 10 illustrates a flowchart of an example method of dispensing medication to a subject via a trial EDC illustrated in FIG. 1.

FIG. 10 illustrates a flowchart of an example method 1000 for dispensing medication to a subject via the trial EDC 176 illustrated in FIG. 1. The method 1000 starts at operation 1002 where a trial site (e.g., trial site 114) has logged on via the trial administration system 104. At operation 1004, a trial ID, site ID, subject ID and visit ID associated with a clinical are received for a subject of the logged on trial site.

At operation 1006, a dispense trigger is received from the trial site, such as programmatically upon randomization of the subject via randomization CF 186 for the first visit or via user-initiated input for subsequent visits. If not trigged, the method 1000 waits until a dispense trigger is received.

At operation 1008, a visit record (visit ID) and dispense indication are added to the trial database 178 for the subject ID. At operation 1010, the trial ID, site ID, subject ID and visit ID are converted via a dispense CF 188 to RTSM dispense data. The RTSM data is transmitted to the article dispenser 164 of RTSM system 120 at operation 1012.

At operation 1014, a set of one or more unit indicators to be dispensed to the subject ID is received from the RTSM system 120. Thereafter, at operation 1016, the dispensed set of unit indicators is stored to the visit record for the subject ID. The method ends at operation 1018.

FIG. 11 illustrates an example webpage to configure a randomization design for a clinical trial. The example webpage can be generated by the randomization designer 126 of the RTSM system 120. As illustrated in the web page, the trial planner 110 can configure the number of arms in the clinical trial and ratio of subjects across the arms. The trial planner 110 can further configure randomization factors and their weights for the clinical trial. The trial planner 110 can also configured the second-best probability for randomization and strata associated with the randomization factors in the clinical trial.

FIG. 12 illustrates an example webpage to setup and simulate the randomization design for a clinical trial. The example webpage can be generated by the simulation module 140 of the randomization simulator 138. The simulations can be executed by the execution module 142. The simulation can be used to minimize the number of subjects in the clinical trial. Multiple simulations can be setup and simulated, as illustrated in FIG. 12.

FIG. 13 illustrates an example webpage to display simulation results of one or more simulations executed in FIG. 12. The example webpage can be generated by the results module 144 of the randomization simulator 138. The displayed results can include for each simulation executed, its simulation metrics, start time and end time, total execution time.

FIG. 14A illustrates an example webpage to display aggregate subject arm assignment within a particular run of a simulation. The example webpage can be generated by the analysis module 146 of the randomization simulator 138. For a particular run shown in FIG. 14, in each of the subject groups the following information is provided: i) a number of simulated subjects in that group that were assigned to each arm; ii) an absolute value of the difference between that number and the total number of subjects in that group, multiplied by a ratio of subjects that should be in each arm given the arm's weights; iii) whenever the absolute value in (ii) is greater than 1, cells with imbalance are identified.

As shown, the subject groups are: 1) subject population of the whole clinical trial; 2) subject population of each trial site; 3) subjects that share a state of a factor (for each factor); and 4) subjects that share a stratum (for each stratum).

FIG. 14B illustrates an example webpage to display aggregate statistical results across runs of a randomization simulation. The aggregate statistical analysis shows for each of the subject groups and each of the arms the mean and standard deviation as well as the minimum number of the subjects from that subject group assigned to that arm. In addition, for each of the subject groups it shows the number of runs that were out of balance.

FIG. 15 illustrates an example webpage to configure the treatment design for a clinical trial. The example web page can be generated by the treatment designer 148. The webpage enable definition of article types and treatments for the clinical trial.

FIG. 16 illustrates an example webpage to manage article types illustrated in FIG. 15. For a given article type illustrated in FIG. 15, dispensation metrics shown can be defined as illustrated in FIG. 16. The example web page can also be generated by the treatment designer 148.

FIG. 17A illustrates an example webpage generated for a clinical trial to manage one or more trial sites. The example webpage can be generated by the site module 168. For each trial site, the webpage displays a study name, trial site number (site ID), country, depot, supply plan, number of subjects randomized to the trial site, number of shipments to the trial site, number of inventory items at the trial site, as well as shipping status. FIG. 17 further illustrates that a supply plan and/or a depot can be assigned to a trial site. Moreover, shipping can also be activated/deactivated for the trial site.

FIG. 17B illustrates an example webpage to assign a supply plan to one or more selected trial sites of the clinical trial. The trial sites for which the supply plan is to be updated (or changed) can be selected in FIG. 17A via check boxes illustrated next to the names of the trial sites. As illustrated in FIG. 17B, the "medium enrollers" supply plan is chosen and reflected for the selected "Balance study site 3" illustrated in FIG. 17A. As further illustrated in FIG. 17A, the "high enrollers" study plan was associated with the trial sites "site 1" and "site 2".

Figure 17C:
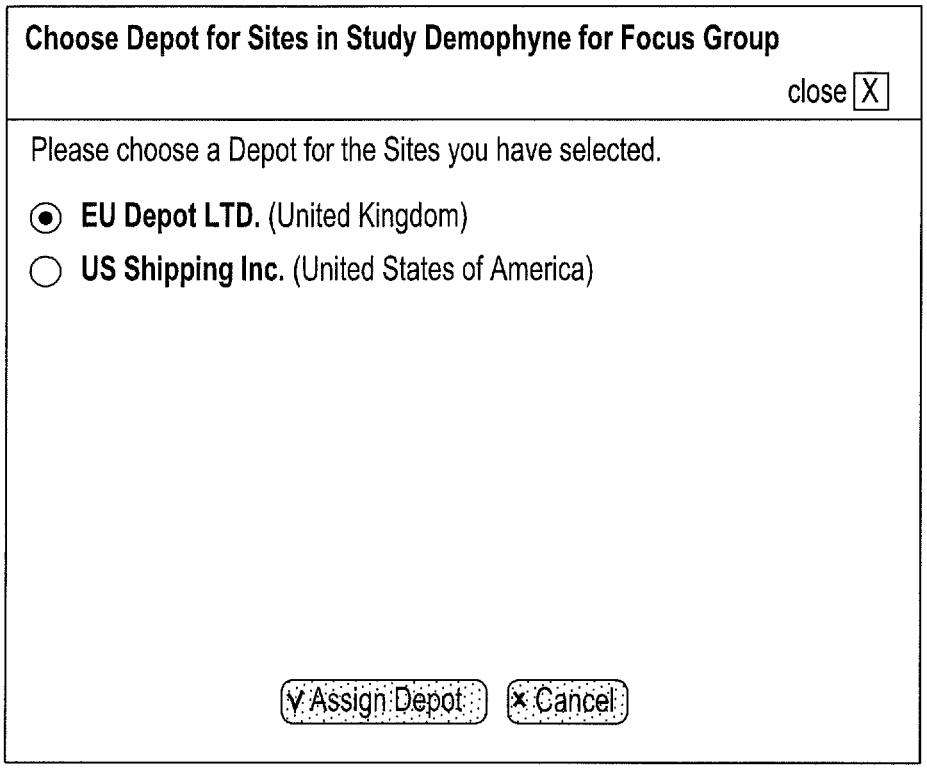
FIG. 17C illustrates an example webpage to assign a depot to one or more selected trial sites of the clinical trial.

FIG. 17C illustrates an example webpage to assign a depot to one or more selected trial sites of the clinical trial. The trial sites for which the depot is to be updated (or changed) can be selected in FIG. 17A via check boxes illustrated next to the next to the names of the trial sites. As illustrated in FIG. 17C, the "EU Depot LTD. United Kingdom" depot is chosen and this depot is associated with the selected "Balance study site 3" illustrated in FIG. 17A.

FIG. 18 illustrates an example webpage generated for management of subjects in a clinical trial. The example webpage can be generated by the subject module 170. For each subject ID, the webpage can include stratus, site, assigned study arm, and randomization time. Other detail can be displayed for the subjects in the example webpage illustrated in FIG. 18.

FIG. 19 illustrates an example webpage for management of one or more article shipments in a clinical trial. The example webpage can be generated by generated by the shipment module 172. Each shipment can include a name of the shipment, status, time status was changes, trial site, depot, tracking number associated with shipment (is status is "shipped"), and units of articles (items of inventory).

FIG. 20 illustrates an example webpage for managing one or more items of inventory in a clinical trial. The example webpage can be generated by generated by the inventory module 174. Each item is identified by an item number and can include a status, trial site, depot, subject, visit, shipment, inventory batch to which the item belongs, article type associated with the item, sequence and location.

FIG. 21 illustrates an example webpage for managing an inventory batch list for a clinical trial. These inventory batches are lists of inventory items (e.g., collected in comma separated value (CSV) format) that a study manager 111 or shipper manager 113 can upload to the RTSM system 120. The inventory batch includes batch name, article type, expiry date, additional batch identifier, notes, depot, and number of items in the batch. When a list (or file) is uploaded RTSM system 120, the inventor module 174 processes the list and enters the articles as well as associated information into the runtime database 158.

FIG. 22 illustrates an example webpage for managing logistics supply plan. The example webpage illustrates the details of specific supply plans and be used to add, change and delete supply plans. Two defined supply plans are shown: medium enrollers and high enrollers. For each plan, there can be defined a supply plan name, article type, minimal number of days between dispensing and expiration, minimal number of days between shipping and expiration, initial trial site stocking level, trial site restocking threshold, trial site restocking level and number of trial sites associated with the supply plan.

FIG. 23 is a block diagram of a general computer system 2300. The computer system 2300 can include a set of instructions that can be executed to cause the computer system 2300 to perform any one or more of the methods or computer based functions disclosed herein with respect to FIGS. 1-22. The computer system 2300 or any portion thereof, may operate as a standalone device or may be connected (e.g., using a network 2324) to other computer systems or devices disclosed herein with respect to FIGS. 1-22. For example, the computer system 2300 can include or be included within any one or more of the computing devices or system in FIG. 1, or any other devices or systems disclosed herein with respect to FIGS. 1-22.

In a networked deployment, the computer system 2300 may operate in the capacity of a server or a client machine in a server-client network environment, or a peer machine in a peer-to-peer (or distributed) network environment. The computer system 2300 can also be implemented as or incorporated into various devices, such as a personal computer (PC), a tablet PC, a personal digital assistant (PDA), a web appliance, a communications device, a mobile device, a wireless telephone, a server, a client or any other machine capable of executing a set of instructions (sequential or otherwise) that specify actions to be taken by that machine. Further, while a single computer system 2300 is illustrated, the term "system" shall also be taken to include any collection of systems or sub-systems that individually or jointly execute a set, or multiple sets, of instructions to perform one or more computer functions.

As illustrated in FIG. 23, the computer system 2300 can include a processor 2302, e.g., a central processing unit (CPU), a graphics-processing unit (GPU), or both. Moreover, the computer system 2300 can include a main memory 2304 and a static memory 2306 that can communicate with each other via a bus 2326. As shown, the computer system 2300 may further include a video display unit 2310, such as a liquid crystal display (LCD), an organic light emitting diode (OLED), a flat panel display, a solid state display, or a cathode ray tube (CRT). Additionally, the computer system 2300 may include an input device 2312, such as a keyboard, and a cursor control device 2214, such as a mouse. The computer system 233300 can also include a disk drive unit 2316, a signal generation device 2322, such as a speaker or remote control, and a network interface device 2308.

In a particular embodiment, as depicted in FIG. 23, the disk drive unit 2316 may include a machine or computer-readable medium 2218 in which one or more sets of instructions 2320 (e.g., software) can be embedded. Further, the instructions 2320 may embody one or more of the methods or logic as described herein with reference to FIGS. 1-22. In a particular embodiment, the instructions 2320 may reside completely, or at least partially, within the main memory 2304, the static memory 2306, and/or within the processor 2302 during execution by the computer system 2300. The main memory 2304 and the processor 2302 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with the various embodiments, the methods described herein may be implemented by software programs that are tangibly embodied in a processor-readable medium and that may be executed by a processor. Further, in an example, non-limited embodiment, implementations can include distributed processing, component/object distributed processing, and parallel processing. Alternatively, virtual computer system processing can be constructed to implement one or more of the methods or functionality as described herein.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

In accordance with various embodiments, the methods described herein may be implemented as one or more software programs running on a computer processor. Dedicated hardware implementations including, but not limited to, application specific integrated circuits, programmable logic arrays and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software which implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein, and other equivalents and successor media, in which the software implementations herein may be stored.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

Thus, a distributed clinical trial system has been described. Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. A method of randomizing subjects in a multi-arm clinical trial, the method comprising:
   receiving, by a computing system, a subject identifier, a trial identifier, and a value associated with a state of a subject in at least one randomization factor from an electronic data capture system that assigns the subject identifier to enroll the subject into the multi-arm clinical trial, the trial identifier associated with the multi-arm clinical trial into which the subject is enrolled, the subject identifier indicating the subject enrolled by the electronic data capture system in the multi-arm clinical trial;
   selecting at runtime, by the computing system, from a database that stores a plurality of randomization design algorithms associated with respective trial identifiers for a plurality of multi-arm clinical trials, a randomization design algorithm previously configured for the multi-arm clinical trial using the trial identifier received from the electronic data capture system; and
   executing, by the computing system, the randomization design algorithm using the value associated with the state of the subject in the at least one randomization factor that randomizes the subject to an arm of the multi-arm clinical trial, the randomization design algorithm assigning the subject identifier to an arm identifier that indicates the arm of the multi-arm clinical trial to which the subject has been randomized in accordance with the randomization design algorithm for the multi-arm clinical trial.

2. The method of claim 1, further comprising transmitting an assignment indicator to the electronic data capture system, the assignment indicator indicating that the subject has been randomized.

3. The method of claim 1, wherein the subject identifier and the trial identifier are received from a randomization custom function of the electronic data capture system.

4. The method of claim 1, further comprising maintaining the trial identifier, subject identifier and arm identifier for the clinical trial in a runtime database.

5. The method of claim 1, further receiving a trial site identifier that indicates the trial site in which the subject enrolled in the clinical trial.

6. The method of claim 5, wherein assigning the subject identifier comprises for each arm in the multi-arm clinical trial:
   determining a trial imbalance in subjects assigned in the multi-arm clinical trial when the subject is randomized to a selected arm of the multi-arm clinical trial;
   determining a site imbalance in subjects assigned to the selected arm;

determining for each of the at least one randomization factor, a state imbalance in subjects in the multi-arm clinical trial that share the state with the subject;

determining strata imbalance in subjects in the multi-arm clinical trial that share the strata with the subject; and generating a weighted sum of imbalances.

7. The method of claim 6, wherein assigning the subject identifier further comprises:

determining that there are two or more arms with a lowest weighted sum of imbalances; and assigning randomly the subject identifier to one of the two or more arms with the lowest weighted sum of imbalances.

8. The method of claim 6, wherein assigning the subject identifier further comprises:

determining that there is one arm with a lowest weighted sum of imbalances;

determining a set of one or more arms with a next lowest weighted sum of imbalances; and assigning randomly the subject identifier to one arm from the one arm with the lowest weighted sum of imbalances and the set of one or more arms with the next lowest weighted sum of imbalances.

9. The method of claim 8, wherein assigning randomly the subject identifier comprises:

determining whether a second-best probability percentage has been defined in the randomization design algorithm; and assigning randomly the subject identifier to the one arm in the set of one or more arms with the next with lowest weighted sum of imbalances in accordance with the defined second-best probability percentage.

10. The method of claim 1, further comprising:

receiving one or more simulation metrics associated with the randomization design algorithm, the randomization design algorithm including one or more randomization metrics; and executing a simulation of the randomization design algorithm based on the one or more simulation metrics before assigning the subject identifier to the arm identifier.

11. The method of claim 10, further comprising:

adjusting at least one of the one or more randomization metrics in the randomization design algorithm; and executing a simulation of the randomization design algorithm based on the one or more randomization metrics as adjusted before assigning the subject identifier to the arm identifier, the randomization design algorithm reducing a number of subjects necessary for multi-arm clinical trial.

12. A system to randomize subjects in a multi-arm clinical trial, the system comprising:

a computing device; and a machine-readable medium comprising instructions that, when executed by the computing device, cause the computing device to perform operations comprising:

receiving a subject identifier, a trial identifier, and a value associated with a state of a subject in at least one randomization factor from an electronic data capture system that assigns the subject identifier to enroll the subject into the multi-arm clinical trial, the trial identifier associated with the multi-arm clinical trial into which the subject is enrolled, the subject identifier indicating the subject enrolled by the electronic data capture system in the multi-arm clinical trial;

selecting at runtime from a database that stores a plurality of randomization design algorithms associated with respective trial identifiers for a plurality of multi-arm clinical trials, a randomization design algorithm previously configured for the multi-arm clinical trial using the trial identifier received from the electronic data capture system; and executing the randomization design algorithm using the value associated with the state of the subject in the at least one randomization factor that randomizes the subject to an arm of the multi-arm clinical trial, the randomization design algorithm assigning the subject identifier to an arm identifier that indicates the arm of the multi-arm clinical trial to which the subject has been randomized in accordance with the randomization design algorithm for the multi-arm clinical trial.

13. The system of claim 12, wherein the operations further comprise transmitting an assignment indicator to the electronic data capture system, the assignment indicator indicating that the subject has been randomized.

14. The system of claim 12, wherein the subject identifier and the trial identifier are received from a randomization custom function of the electronic data capture system.

15. The system of claim 12, further comprising a runtime database configured to maintain the trial identifier, subject identifier and arm identifier for the clinical trial.

16. The system of claim 12, wherein the operations further comprise receiving a trial site identifier that indicates the trial site in which the subject enrolled in the clinical trial.

17. The system of claim 16, wherein for each arm in the multi-arm clinical trial the operations further comprise:

determining a trial imbalance in subjects assigned in the multi-arm clinical trial when the subject is randomized to a selected arm of the multi-arm clinical trial;

determining a site imbalance in subjects assigned to the selected arm;

determining for each of the at least one randomization factor, a state imbalance in subjects in the multi-arm clinical trial that share the state with the subject;

determining strata imbalance in subjects in the multi-arm clinical trial that share the strata with the subject; and generating a weighted sum of imbalances.

18. The system of claim 17, wherein the operations further comprise:

determining that there are two or more arms with a lowest weighted sum of imbalances; and assigning randomly the subject identifier to one of the two or more arms with the lowest weighted sum of imbalances.

19. The system of claim 17, wherein the operations further comprise:

determining that there is one arm with a lowest weighted sum of imbalances;

determining a set of one or more arms with a next lowest weighted sum of imbalances; and assigning randomly the subject identifier to one arm from the one arm with the lowest weighted sum of imbalances and the set of one or more arms with the next lowest weighted sum of imbalances.

20. The system of claim 19, wherein the operations further comprise:

determining whether a second-best probability percentage has been defined in the randomization design algorithm; and assigning randomly the subject identifier to the one arm in the set of one or more arms with the next with lowest weighted sum of imbalances in accordance with the defined second-best probability percentage.

21. The system of claim 12, wherein the operations further comprise:
  receiving one or more simulation metrics associated with the randomization design algorithm, the randomization design algorithm including one or more randomization metrics; and
  executing a simulation of the randomization design algorithm based on the one or more simulation metrics before assigning the subject identifier to the arm identifier.

22. The system of claim 21, wherein the operations further comprise:
  adjusting at least one of the one or more randomization metrics in the randomization design algorithm; and
  executing a simulation of the randomization design algorithm based on the one or more randomization metrics as adjusted before assigning the subject to the arm identifier, the randomization design algorithm reducing a number of subjects necessary for multi-arm clinical trial.

23. A non-transitory machine-readable storage medium comprising instructions that, when executed by a processor, cause the processor to perform operations comprising:
  receiving a subject identifier, a trial identifier, and a value associated with a state of a subject in at least one randomization factor from an electronic data capture system that assigns the subject identifier to enroll the subject into the multi-arm clinical trial, the trial identifier associated with a multi-arm clinical trial into which the subject is enrolled, the subject identifier indicating the subject enrolled by the electronic data capture system in the multi-arm clinical trial;
  selecting at runtime from a database that stores a plurality of randomization design algorithms associated with respective trial identifiers for a plurality of multi-arm clinical trials, a randomization design algorithm previously configured for the multi-arm clinical trial using the trial identifier received from the electronic data capture system; and
  executing the randomization design algorithm using the value associated with the state of the subject in the at least one randomization factor that randomizes the subject to an arm of the multi-arm clinical trial, the randomization design algorithm assigning the subject identifier to an arm identifier that indicates the arm of the multi-arm clinical trial to which the subject has been randomized in accordance with the randomization design algorithm for the multi-arm clinical trial.

24. The non-transitory machine-readable storage medium of claim 23, wherein the operations further comprise transmitting an assignment indicator to the electronic data capture system, the assignment indicator indicating that the subject has been randomized.

25. The non-transitory machine-readable storage medium of claim 23, wherein the subject identifier and the trial identifier are received from a randomization custom function of the electronic data capture system.

26. The non-transitory machine-readable storage medium of claim 23, wherein the operations further comprise maintaining the trial identifier, subject identifier and arm identifier for the clinical trial in a runtime database.

27. The non-transitory machine-readable storage medium of claim 23, wherein the operations further comprise receiving a trial site identifier that indicates the trial site in which the subject enrolled in the clinical trial.

28. The non-transitory machine-readable storage medium of claim 27, wherein for each arm in the multi-arm clinical trial the operations further comprise:
  determining a trial imbalance in subjects assigned in the multi-arm clinical trial when the subject is randomized to a selected arm of the multi-arm clinical trial;
  determining a site imbalance in subjects assigned to the selected arm;
  determining for each of the at least one randomization factor, a state imbalance in subjects in the multi-arm clinical trial that share the state with the subject;
  determining strata imbalance in subjects in the multi-arm clinical trial that share the strata with the subject; and
  generating a weighted sum of imbalances.

29. The non-transitory machine-readable storage medium of claim 28, wherein the operations further comprise:
  determining that there are two or more arms with a lowest weighted sum of imbalances; and
  assigning randomly the subject identifier to one of the two or more arms with the lowest weighted sum of imbalances.

30. The non-transitory machine-readable storage medium of claim 28, wherein the operations further comprise:
  determining that there is one arm with a lowest weighted sum of imbalances;
  determining a set of one or more arms with a next lowest weighted sum of imbalances; and
  assigning randomly the subject identifier to one arm from the one arm with the lowest weighted sum of imbalances and the set of one or more arms with the next lowest weighted sum of imbalances.

31. The non-transitory machine-readable storage medium of claim 30, wherein the operations further comprise:
  determining whether a second-best probability percentage has been defined in the randomization design algorithm; and
  assigning randomly the subject identifier to the one arm in the set of one or more arms with the next with lowest weighted sum of imbalances in accordance with the defined second-best probability percentage.

32. The non-transitory machine-readable storage medium of claim 23, wherein the operations further comprise:
  receiving one or more simulation metrics associated with the randomization design algorithm, the randomization design including one or more randomization metrics; and
  execute a simulation of the randomization design algorithm based on the one or more simulation metrics before assigning the subject identifier to the arm identifier.

33. The non-transitory machine-readable storage medium of claim 32, wherein the operations further comprise:
  adjusting at least one of the one or more randomization metrics in the randomization design algorithm; and
  execute a simulation of the randomization design algorithm based on the one or more randomization metrics as adjusted before assigning the subject identifier to the arm identifier, the randomization design algorithm reducing a number of subjects necessary for multi-arm clinical trial.

* * * * *

UNITED STATES PATENT AND TRADEMARK OFFICE
CERTIFICATE OF CORRECTION

| | | |
|---|---|---|
| PATENT NO. | : 8,738,397 B2 | Page 1 of 1 |
| APPLICATION NO. | : 13/157875 | |
| DATED | : May 27, 2014 | |
| INVENTOR(S) | : Young et al. | |

It is certified that error appears in the above-identified patent and that said Letters Patent is hereby corrected as shown below:

IN THE SPECIFICATION:

Column 2, line 13:

Delete: "enrolment"

Insert: -- enrollment --

Column 5, line 32:

Delete: "114, 118, 118"

Insert: -- 114, 116, 118 --

Column 10, line 53:

Delete: "and (2) the supply"

Insert: -- and (ii) the supply --

Signed and Sealed this
Twenty-third Day of September, 2014

Michelle K. Lee
*Deputy Director of the United States Patent and Trademark Office*